(12) United States Patent
Srinivasan et al.

(10) Patent No.: US 11,033,251 B2
(45) Date of Patent: Jun. 15, 2021

(54) SYSTEMS AND METHODS FOR ULTRASOUND IMAGING

(71) Applicant: EDAN INSTRUMENTS, INC., Guangdong (CN)

(72) Inventors: Seshadri Srinivasan, Sunnyvale, CA (US); Jianhua Mo, Palo Alto, CA (US); Ed Gardner, Sunnyvale, CA (US); Feng Ling, Shenzhen (CN); Sean Murphy, Sunnyvale, CA (US)

(73) Assignee: EDAN INSTRUMENTS, INC., Shenzhen (CN)

( * ) Notice: Subject to any disclaimer, the term of this patent is extended or adjusted under 35 U.S.C. 154(b) by 77 days.

(21) Appl. No.: 16/407,312

(22) Filed: May 9, 2019

(65) Prior Publication Data

US 2019/0261956 A1 Aug. 29, 2019

Related U.S. Application Data

(63) Continuation of application No. PCT/CN2016/105158, filed on Nov. 9, 2016.

(51) Int. Cl.
*G06K 9/00* (2006.01)
*A61B 8/08* (2006.01)
(Continued)

(52) U.S. Cl.
CPC .......... *A61B 8/5269* (2013.01); *A61B 8/5215* (2013.01); *A61B 8/5292* (2013.01);
(Continued)

(58) Field of Classification Search
CPC ..... A61B 8/5269; A61B 8/5292; A61B 8/565; A61B 8/5215; G06T 5/001; G06T 7/11;
(Continued)

(56) References Cited

U.S. PATENT DOCUMENTS 6,501,849 B1 12/2002 Gupta et al.
6,754,556 B1 * 6/2004 Landers ............. G05B 19/4097
700/182

(Continued)

FOREIGN PATENT DOCUMENTS

CN 104281997 A 1/2015
CN 104778036 A 7/2015
(Continued)

OTHER PUBLICATIONS

International Search Report in PCT/CN2016/105158 dated Jul. 27, 2017, 4 pages.
(Continued)

*Primary Examiner* — Amir Alavi

(57) ABSTRACT

A computing system includes a memory configured to store instructions, and one or more processors configured to execute the instructions to receive data relating to an image or a user, determine a feature from the data, identify a user preference from a user profile, obtain a model, and segment the image based on the feature, the user preference, and the model. The model is generated by determining a historical feature from historical data as an input, determining a desired output, obtaining a preliminary model based on the input and the desired output, determining an actual output of the preliminary model, determining error criteria between the actual output and the desired output, and generating the model by updating the preliminary model based on the error criteria.

11 Claims, 21 Drawing Sheets

(51) Int. Cl.
*G06T 7/11* (2017.01)
*G16H 50/20* (2018.01)
*G16H 30/40* (2018.01)
*A61B 8/00* (2006.01)
*G06T 5/00* (2006.01)
*G06K 9/62* (2006.01)
*G01S 7/00* (2006.01)
*G01S 7/52* (2006.01)
*G06K 9/36* (2006.01)
*G06K 9/46* (2006.01)
*G06T 7/10* (2017.01)

(52) U.S. Cl.
CPC .............. *A61B 8/565* (2013.01); *G01S 7/003* (2013.01); *G01S 7/52084* (2013.01); *G01S 7/52098* (2013.01); *G06K 9/36* (2013.01); *G06K 9/4604* (2013.01); *G06K 9/6218* (2013.01); *G06K 9/6267* (2013.01); *G06T 5/00* (2013.01); *G06T 5/001* (2013.01); *G06T 7/10* (2017.01); *G06T 7/11* (2017.01); *G16H 30/40* (2018.01); *G16H 50/20* (2018.01); *G06K 2209/05* (2013.01); *G06T 2207/10132* (2013.01); *G06T 2207/20008* (2013.01); *G06T 2207/20081* (2013.01)

(58) Field of Classification Search
CPC . G06T 2207/20008; G06T 2207/10132; G06T 2207/20081; G16H 30/40; G16H 50/20; G06K 9/6218; G06K 9/4604
See application file for complete search history.

(56) References Cited

U.S. PATENT DOCUMENTS

| | | | | |
|---|---|---|---|---|
| 7,280,704 | B2* | 10/2007 | Peli | G06T 5/10 |
| | | | | 382/254 |
| 8,184,901 | B2* | 5/2012 | Edgar | G06T 7/11 |
| | | | | 382/162 |
| 8,634,673 | B1 | 1/2014 | McDougal et al. | |
| 9,824,492 | B2* | 11/2017 | Peterson | G06T 19/20 |
| 10,453,252 | B2* | 10/2019 | Chapman | G06T 17/00 |
| 10,467,757 | B2* | 11/2019 | Wang | G06K 9/627 |
| 10,740,914 | B2* | 8/2020 | Xiao | G01S 17/08 |
| 2006/0253296 | A1 | 11/2006 | Liisberg et al. | |
| 2010/0106499 | A1* | 4/2010 | Lubowich | G10L 15/005 |
| | | | | 704/235 |
| 2017/0361076 | A1* | 12/2017 | Zhou | G16H 20/13 |
| 2019/0261956 | A1* | 8/2019 | Srinivasan | A61B 8/5292 |

FOREIGN PATENT DOCUMENTS

| | | |
|---|---|---|
| CN | 105224184 A | 1/2016 |
| CN | 105761229 A | 7/2016 |
| CN | 105825484 A | 8/2016 |

OTHER PUBLICATIONS

Written Opinion in PCT/CN2016/105158 dated Jul. 27, 2017, 4 pages.
Chinese First office action,Chinese application No. 201680003948.X, dated Aug. 31, 2020 (8 pages).

* cited by examiner

SYSTEMS AND METHODS FOR ULTRASOUND IMAGING

CROSS-REFERENCE TO RELATED APPLICATION

This application is a continuation of International Application No. PCT/CN2016/105158, field on Nov. 9, 2016, the contents of which are hereby incorporated by reference.

TECHNICAL FIELD

The present disclosure generally relates to systems and methods for processing medical imaging, and more particularly, to systems and methods for ultrasound imaging.

BACKGROUND

Conventional ultrasound imaging systems typically have a static system configuration where the system does not adapt to the user preferences or the image content. System updates are infrequent and typically occur on a release basis. This results in sub-optimized image processing and a heavy dependence on the user's skill. Methods and systems for processing images in ultrasound systems for automatically segmenting images, enhancing the image quality, improving the workflow, and adapting the user-interface are proposed.

SUMMARY

One aspect of the present disclosure is directed to a computing system for ultrasound imaging. The computing system includes a memory configured to store instructions and a user profile. The computing system also includes one or more processors configured to execute the instructions to receive data relating to an image or a user, determine one or more features from the data, identify one or more user preferences from a user profile, obtain a model, and segment the image into at least one segment or enhance the image or modify a user interface or modify a workflow based on at least one of the one or more features, at least one of the one or more user preferences, and the model. The model is generated according to a process including the following steps: determining one or more historical features from historical data as an input, determining a desired output, obtaining a preliminary model based on the input and the desired output, determining an actual output of the preliminary model based on the input and the preliminary model, determining error criteria between the actual output of the preliminary model and the desired output, and generating the model by updating the preliminary model based on the error criteria.

Another aspect of the present disclosure is directed to a method for ultrasound imaging. The method includes receiving data relating to an image or a user, determining one or more features from the data, identifying one or more user preferences from a user profile, obtaining a model, and segmenting the image into at least one segment or enhancing the image or modifying a user interface or modifying a workflow based on at least one of the one or more features, at least one of the one or more user preferences, and the model. The model is generated based on a process including the following steps: determining one or more historical features from historical data as an input, determining a desired output, obtaining a preliminary model based on the input and the desired output, determining an actual output of the preliminary model based on the input and the preliminary model, determining error criteria between the actual output of the preliminary model and the desired output, and generating the model by updating the preliminary model based on the error criteria.

Yet another aspect of the present disclosure is directed to a non-transitory computer readable medium embodying a computer program product, the computer program product comprising instructions configured to cause a computing system to receive data relating to an image or a user, determine one or more features from the data, identify one or more user preferences from a user profile, obtain a model, and segment the image into at least one segment or enhance the image or modify a user interface or modify a workflow based on at least one of the one or more features, at least one of the one or more user preferences, and the model. The model is generated based on a process having the following steps: determining one or more historical features from historical data as an input, determining a desired output, obtaining a preliminary model based on the input and the desired output, determining an actual output of the preliminary model based on the input and the preliminary model, determining error criteria between the actual output of the preliminary model and the desired output, and generating the model by updating the preliminary model based on the error criteria.

BRIEF DESCRIPTION OF THE DRAWINGS

The present disclosure is further described in terms of exemplary embodiments. The foregoing and other aspects of embodiments of present disclosure are made more evident in the following detail description, when read in conjunction with the attached drawing figures.

DETAILED DESCRIPTION

Figure 1:
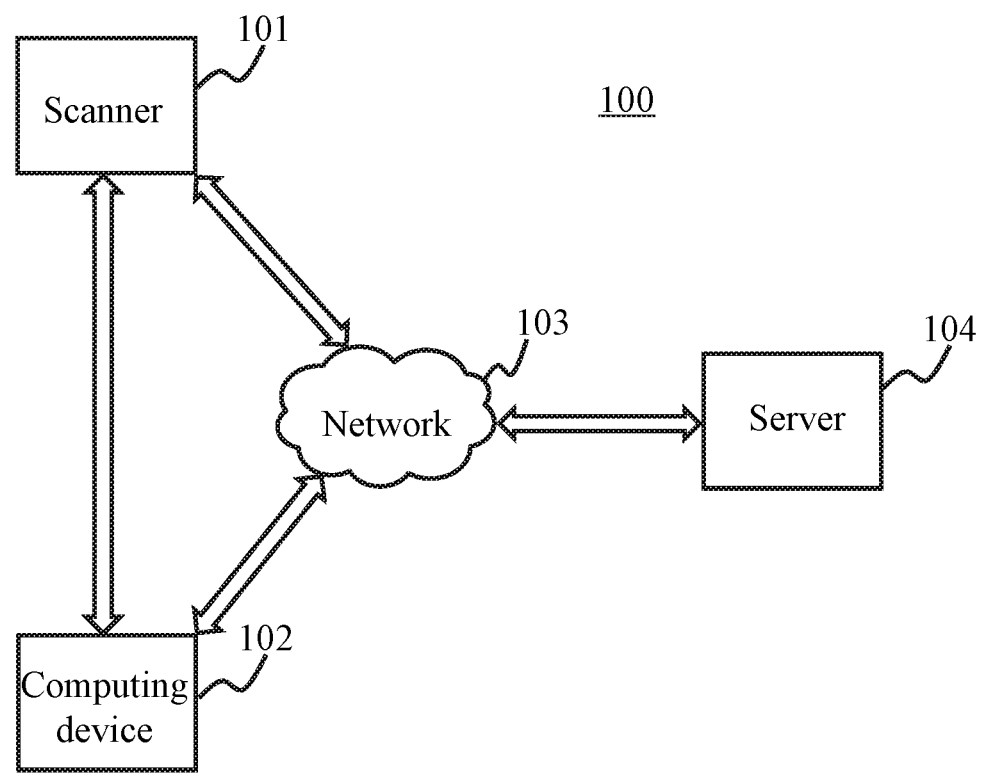
FIG. 1 is a block diagram of an exemplary computing system according to some embodiments.

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular example embodiments only and is not intended to be limiting. As used herein, the singular forms "a," "an" and "the" may be intended to include the plural forms as well, unless the context clearly indicates otherwise. It will be further understood that the terms "comprises," "comprising," "includes," and/or "including" when used in this specification, specify the presence of stated features, integers, steps, operations, elements, and/or components, but do not preclude the presence or addition of one or more other features, integers, steps, operations, elements, components, and/or groups thereof.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. It is understood that the drawings are not to scale.

Moreover, while the system and method in the present disclosure is described primarily in regard to ultrasonography imaging systems, it should also be understood that this is only one exemplary embodiment. The system or method of the present disclosure may be applied to any other kind of clinical imaging applications and user interfaces for image processing applications aside from ultrasound imaging.

The term "user" may refer to an operator, or a group of operators that operate a system or method described in the present disclosure. Merely by way of example, the user may be a doctor, a nurse, a medical examiner, or any other person using the system or the method described in this application. The term "patient" may refer to one or more human beings or animals for scanning. The term "feature" may refer to any individual measurable property of a phenomenon being observed.

FIG. 1 is a block diagram of an exemplary computing system 100 according to some embodiments. Computing system 100 may be used in different scenarios, including but not limited to healthcare, industry, environment, military, and security, etc. As illustrated in FIG. 1, computing system 100 may include a scanner 101, a computing device 102, a network 103, and a server 104. In some embodiments, one or more components in computing system 100 (e.g., scanner 101, computing device 102, and server 104) may transmit information and/or data to other component(s) in computing system 100 via network 103.

In some embodiments, scanner 101 may be configured to scan a subject and acquire data relating to the subject. The subject may be any object for scanning. Merely by of example, the subject may include a human, an animal, a plant, a device, a body, an organ, a tissue, or the like, or any combination thereof. In some embodiments, scanner 101 may include an X-ray radiography scanner, a magnetic resonance imaging (MRI) scanner, an ultrasound (ultrasonography) scanner, an ultrasound probe, an ultrasound transducer, an endoscopy scanner, an elastography scanner, a tactile imaging scanner, a thermography scanner, a computed tomography (CT) scanner, a positron emission tomography (PET) scanner, a single photon emission computed tomography (SPECT) scanner, a digital subtraction angiography (DSA) scanner, a multimodal imaging scanner, an electroencephalography (EEG) scanner, a magnetoencephalography (MEG) scanner, or the like, or any combination thereof. Exemplary multimodal imaging scanner may include a positron emission tomography—computed tomography (PET-CT) scanner, a positron emission tomography—magnetic resonance imaging (PET-MRI) scanner, etc. In some embodiments, scanner 101 may include a digital camera, a web camera, a smartphone, a tablet, a laptop, a video gaming console equipped with a web camera, a wearable sensor, an embedded sensor, or the like. Scanner 101 may monitor or scan the subject periodically, continuously, or on demand.

Figure 2:
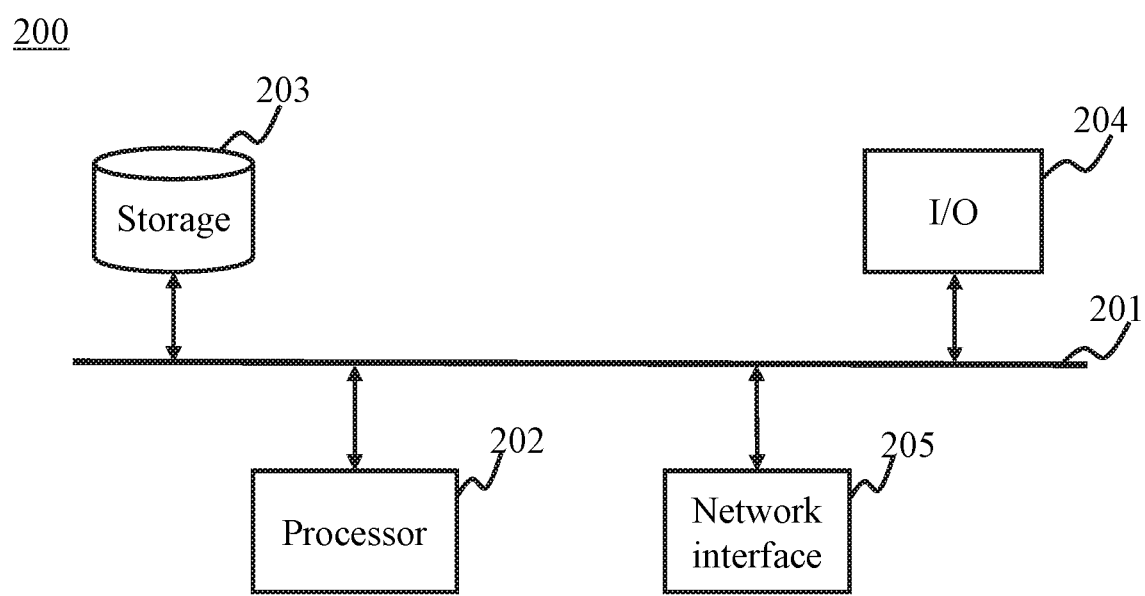
FIG. 2 is a block diagram of an exemplary device in the computing system illustrated in FIG. 1 according to some embodiments.

In some embodiments, computing device 102 may be configured to process the data acquired from scanner 101 of the subject. Computing device 102 may also store data, instructions, algorithms, user profiles, models, or the like, relating to an examination of the subject. Computing device 102 may also include a display to present one or more images and a graphical user interface (GUI) to user. In some embodiments, computing device 102 may include a desktop computer, a laptop computer, a mobile phone, a phablet, a tablet computer, a personal digital assistant (PDA), an embedded device, a wearable device, or the like. Exemplary wearable device may include a smart bracelet, a smart watch, a smart glass, a smart helmet, a smart clothing, etc. In some embodiments, computing device 102 may be implemented on a computing platform having components as illustrated in FIG. 2 in the present disclosure.

In some embodiments, computing device 102 may be a combination of a plurality of components residing in separate enclosures or housings, configured to perform the functions thereof disclosed in this application. In some embodiments, the components may be deployed in parallel, in series, co-hosted, or the like, or a combination thereof.

In some embodiments, computing device 102 may include a plurality of partitions configured to perform one or more functions of thereof disclosed in this application. The partitions of computing device 102 may be co-hosted or hosted at different locations. In some embodiments, the partitions of computing device 102 may be deployed in parallel, in series, or the like, or a combination thereof.

In some embodiments, one or more components of computing device 102 may be integrated with scanner 101, configured to perform one or more functions of computing device 102 and scanner 101 disclosed in this application.

In some embodiments, server 104 may be configured to process the data of the subject acquired from scanner 101 and/or computing device 102. Server 104 may also store data, instructions, algorithms, user profiles, models, or the like, relating to an examination of the subject. In some embodiments, server 104 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, server 104 may be implemented on a computing platform having components as illustrated in FIG. 2 in the present disclosure.

In some embodiments, scanner 101 and computing device 102 may be packaged in a single device configured to implement functions of both scanner 101 and computing device 102 described elsewhere in the present disclosure. For example, scanner 101 and computing device 102 may directly connected as an all-in-one machine. In some embodiments, computing device 102 and server 104 may be packaged in a single device configured to implement functions of both scanner 101 and computing device 102 described elsewhere in the present disclosure. In some embodiments, computing system 100 may not include server 104. Computing device 102 may be configured to implement functions described elsewhere in the present disclosure locally. In some embodiments, computing system 100 may not include computing device 102. Server 104 may be configured to implement functions described elsewhere in the present disclosure.

In some embodiments, network 103 may be configured to facilitate information and/or data exchange among the components of computing system 100. For example, scanner 101 may capture one or more images and transmit the image(s) to computing device 102 via network 103. Computing device 102 may access the data from server 104 via network 103. In some embodiments, the image may be a still image, animated image, or motion pictures (videos, clips, etc.). In some embodiments, network 103 may be any type of wired or wireless network. Merely by way of example, network 103 may include a cable network, a wireline network, an optical fiber network, a tele communications network, an intranet, an Internet, a local area network (LAN), a wide area network (WAN), a wireless local area network (WLAN), a metropolitan area network (MAN), a wide area network (WAN), a Bluetooth network, a ZigBee network, a near field communication (NFC) network, or the like, or any combination thereof.

In some embodiments, server 104 may store data, instructions, algorithms, user profiles, models, etc., for computing device 102 and/or scanner 101 to perform one or more functions described elsewhere in this disclosure. Server 104 may also update the data, instructions, algorithms, user profiles, models, etc. The update may be scheduled (e.g., periodically) or on-demand in response to a request by scanner 101 or computing device 102. Scanner 101 and/or computing device 102 may access the updated data, instructions, algorithms, user profiles, models, etc., and scanner 101 via network 103. In some embodiments, one or more processes described in the present disclosure may be implemented in a single component (e.g., in computing device 102 or server 104, etc.). In some embodiments, a process described in the present disclosure may be completed cooperatively by two or more components. In some embodiments, one or more processes (e.g., generating a model, segmenting an image, enhancement an image, adjusting workflow and/or adjusting user interface, etc.) may be implemented in computing device 102 and/or in server 104. For example, one or more processes (e.g., generating a model, segmenting an image, enhancement an image, adjusting workflow and/or adjusting user interface, etc.) may be implemented on a cloud including one or more servers 104. As another example, one or more processes (e.g., generating a model, segmenting an image, enhancement an image, adjusting workflow and/or adjusting user interface, etc.) may be implemented locally on computing device 102.

In some embodiments, server 104 may provide an update for updating the model(s) described in this application (e.g. image enhancement model, image segmentation model, user interface model, workflow model, etc.) to scanner 101 and/or computing device 102. Server 104 may push the update to scanner 101 and/or computing device 102 periodically. Alternatively or additionally, scanner 101 and/or computer device may request the update from server 104 (on demand or periodically). In some embodiments, the period of the periodic updates may be determined according to the components of system (e.g., scanner 101, computing device 102, server 104, etc.), the user(s), the examination, etc. For example, server 104 may update the models, data, instructions, algorithms, user profile after each examination. As another example, server 104 may update the models, data, instructions, algorithms, user profile one hour, once one day, etc.

In some embodiments, a computing device 102 may be in communication with a plurality of scanners 101. The computing device 102 may process data acquired from the scanners 101. In some embodiments, a plurality of computing devices 102 may be in communication with a scanner 101. For example, a first computing device 102 may process the cardiac ultrasound images from the scanner 101, while a second computing device 102 may process the obstetric ultrasound images from the scanner 101.

In some embodiments, a server 104 may be in communication with a plurality of computing device 102. Server 104 may store data, instructions, algorithms, user profiles, models, etc., for the computing device 102. In some embodiments, a plurality of servers 104 may be in communication with a computing device 102. For example, a first server 104 may store the data relating to the images acquired from the computing device 102. A second server 104 may store and/or update user profiles. A third server 104 may store and/or instructions, algorithms and models. Alternatively or additionally, a plurality of servers 104 may process and/or update, cooperatively or independently, update the models, data, instructions, algorithms, user profiles.

FIG. 2 is a block diagram of an exemplary device 200 in computing system 100 illustrated in FIG. 1 according to some embodiments. In some embodiments, computing device 102 and/or server 104 may have similar or the same hardware and/or configuration as device 200 illustrated in FIG. 2, and one or more functions performed by computing device 102 and/or server 104 described in this disclosure may be implemented using similar or the same hardware and/or configuration as device 200.

As illustrated in FIG. 2, device 200 may include a bus 201, a processor 202, a storage 203, an I/O 204, and a network interface 205. Bus 201 may be configured to transfer information and/or data among numerous components of device 200. For example, bus 201 may facilitate communications between processor 202 and storage 203 for exchanging information and/or data. In some embodiments, bus 201 may include a hardware component and/or a software. Exemplary hardware component may include a wire, an optical fiber, a cable, etc. In some embodiments, the software bus may be one or more programs written in one or more programming languages.

Processor 202 may be configured to execute instructions and/or process information and/or data to perform one or more functions described in the present disclosure. Merely by way of example, processor 202 may process image data acquired from scanner 101 of one or more subjects for image segmentation, image enhancement, etc. Processor 202 may also execute instructions for adjusting user interface and/or workflow. In some embodiments, processor 202 may include one or more processors (e.g., single-core processor(s) or multi-core processor(s)). Merely by way of example, processor 202 may include a central processing unit (CPU), an application-specific integrated circuit (ASIC), an application-specific instruction-set processor (ASIP), a graphics processing unit (GPU), a physics processing unit (PPU), a digital signal processor (DSP), a field programmable gate array (FPGA), a programmable logic device (PLD), a controller, a microcontroller unit, a processor, a microprocessor, or the like, or any combination thereof.

Storage 203 may be configured to store data and/or instructions. In some embodiments, storage 203 may include a mass storage, a removable storage, a volatile read-and-write memory, a read-only memory (ROM), or the like, or any combination thereof. Exemplary mass storage may include a magnetic disk, an optical disk, a solid-state drives, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc.

In some embodiments, storage 203 may be configured to store one or more programs and/or instructions that may be executed by processor 202 to perform exemplary methods described in the present disclosure. For example, storage 203 may be configured to store program(s) and/or instruction(s) executed by processor 202 to determine features relating to an image and/or a user as inputs. As another example, storage 203 may be configured to store program(s) and/or instruction(s) executed by processor 202 to determine desired outputs. As still another example, storage 203 may be configured to store program(s) and/or instruction(s) executed by processor 202 to obtain a model using inputs and outputs. As still another example, storage 203 may be configured to store program(s) and/or instruction(s) that may be executed by processor 202 to process the image and/or adjust workflow or user interface based on the model, such as the model for image segmentation, image enhancement, user interface improvement, workflow improvement, etc.

In some embodiments, storage 203 may be configured to store data generated and/or used by processor 202. For example, storage 203 may be configured to store one or more user profiles. Processor 202 may access the user profile(s) stored in storage 203 to identify a user and/or retrieve user preference(s). As another example, storage 203 may be configured to store one or more models. Processor 202 may access the model(s) stored in storage 203 for image segmentation, image enhancement, user interface improvement, workflow improvement, etc. As still another example, storage 203 may be configured to store one or more imaging parameters for image enhancement. Specifically, the imaging parameters may be used for adjusting one or more of contrast, overall brightness, saturation, etc. in images. Processor 202 may access the imaging parameter(s) stored in storage 203 for image enhancement. As still another example, storage 203 may be configured to store features relating to the images and/or users, and/or desired outputs corresponding to the features. Processor 202 may access the features and/or desired outputs stored in storage 203 to obtain the model.

I/O 204 may be configured to receive input information from and/or output information to a user. In some embodiments, I/O 204 may include one or more input devices configured to receive input from a user. Exemplary input device include a keyboard, a mouse, a touch screen, a trackball, a touchpad, a pointing stick, a handwritten input device, an image input device, a voice input device, an electromagnetic wave input device, a gesture input device, a button, a knob, or the like, or any combination thereof. For example, computing system 100 may receive a user's name, a patient's name, a type of the examination type, a protocol or procedure of an examination, etc., through an input device (e.g., a keyboard) operated by a user. As another example, computing system 100 may receive a user login through a biometric identification device, such as, a voice recognition device, a face recognition device, a finger print recognition device, an iris recognition device, etc. As still another example, computing system 100 may receive a user and/or a patient through a barcode or quick response (QR) code scanner.

In some embodiments, I/O 204 may include one or more output devices configured to output information to a user. Output device may be a printer, a display device, a speaker, etc. Exemplary display device may include a liquid crystal display (LCD) panel, a light emitting diode display (LED) panel, an organic light emitting diode (OLED) panel, a cathode ray tube (CRT) display, a plasma display, a virtual display device, the like, or any combination thereof. In some embodiments, I/O 204 may be configured to display an image scanned by scanner 101 and/or a processed image processed by processor 202. In some embodiments, I/O 204 may be configured to display a graphical user interface for the user. In some embodiments, input device and display may be integrated on a single physical device including a capacitive touch screen and a resistive touch screen.

Network interface 205 may be configured to interface with network 103 and/or other devices (e.g., scanner 101, server 104, etc.). In some embodiment, network interface 205 may include a hardware network interface and/or a software network interface. Exemplary hardware network interface may include a copper distributed data interface (CDDI), a fiber distributed data interface (FDDI), an attachment unit interface (AUI), etc. In some embodiments, software network interface may be implemented according to programming and/or computer language(s). Network interface 205 may include circuitry for coupling computing device 102 to one or more networks, and is constructed for use with one or more communication protocols and technologies including, but not limited to, global system for mobile communications (GSM), code-division multiple access (CDMA), time-division multiple access (TDMA), general packet radio service (GPRS), enhanced data rate for GSM evolution (EDGE), wideband code division multiple access (WCDMA), high speed downlink packet access (HSDPA), long term evolution (LTE), user datagram protocol (UDP), transmission control protocol/Internet protocol (TCP/IP), short message service (SMS), wireless application protocol (WAP), ultra wide band (UWB), IEEE 802.16 worldwide interoperability for microwave access (WiMax), session initiated protocol/realtime transport protocol (SIP/RTP), or any of a variety of other wireless communication protocols.

In some embodiments, one or more components in device 200 described above in FIG. 2 may be implemented in an electronic circuitry, a software, a firmware, a hardware, a program, or the like, or any combination thereof. Merely by way of example, processor 202 may be implemented by one or more programs, and storage 203 may be implemented by one or more hardware (e.g., a flash drive, a ROM, a RAM, etc.).

Figure 3:
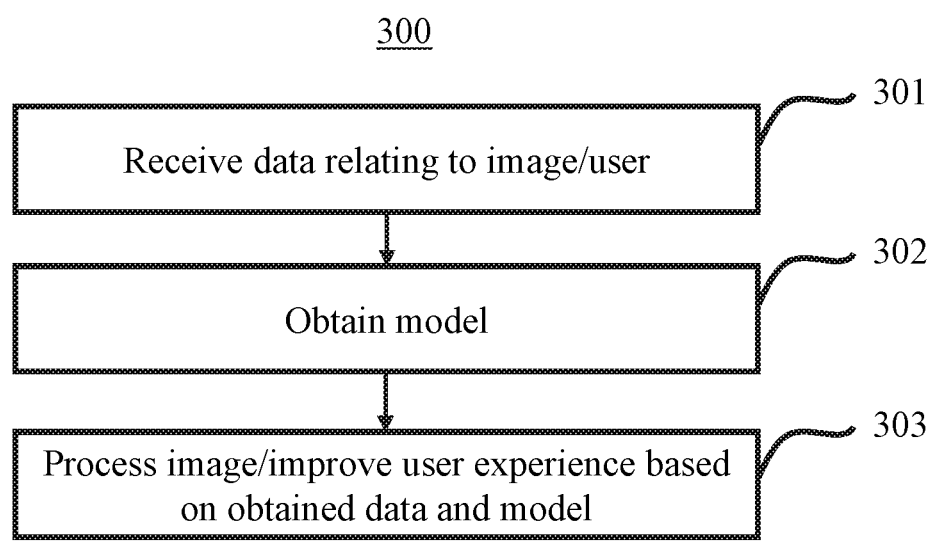
FIG. 3 is a flowchart of an exemplary process of processing an image and/or improving user experience according to some embodiments.

FIG. 3 is a flowchart of an exemplary process 300 of processing an image and/or improving user experience according to some embodiments. Merely by way of example, computing system 100 may implement process 300 in an X-ray radiography, a magnetic resonance imaging (MRI), an ultrasound (ultrasonography), an endoscopy, an elastography, a tactile imaging, a thermography, a computed tomography (CT), a positron emission tomography (PET), a single photon emission computed tomography (SPECT), a digital subtraction angiography (DSA), a multimodal imaging, an electroencephalography (EEG), a magnetoencephalography (MEG), or the like, or any combination thereof. In some embodiments, computing system 100 may implement process 300 for image processing (e.g., image segmentation, image enhancement, image fusion, image compression, etc.), user experience improvement (e.g., user interface adjustment, workflow adjustment, etc.), etc.

At 301, processor 202 may receive data relating to an image, a user, and/or a patient. The date may include an image data, an input instruction from the user, an identification of the user and/or patient, information relating to an examination, or the like, or any combination thereof.

At 302, processor 202 may obtain a model. In some embodiments, the model may include a method, an algorithm, a process, a formula, a rule, or the like, or any combination thereof. Merely by way of example, the model may include a segmentation model, an enhancement model, a user interface model, a workflow model, or the like, or any combination thereof. In some embodiments, the model may include a feed-forward neural network (FNN), a recurrent neural network (RNN), a Kohonen self-organizing map, an autoencoder, a probabilistic neural network (PNN), a time delay neural network (TDNN), a radial basis function network (RBF), a learn vector quantization, a convolutional neural network (CNN), an adaptive linear neuron (ADALINE) model, an associative neural network (ASNN), or the like, or any combination thereof. Exemplary recurrent neural network (RNN) may include a Hopfield network, a Boltzmann machine, an echo state network, a long short term memory network, a Bi-directional RNN, a hierarchical RNN, a stochastic neural networks, or the like, or any combination thereof.

In some embodiments, processor 202 may classify one or more users into one or more classes. The classification of a user may be based on the user's usage patterns in the workflow, demographics, proficiency, location, age, educational background, physical condition, mental condition, or the like, or the combination thereof. In some embodiments, processor 202 may utilize a clustering method when classifying users into classes. The clustering method may include a hierarchical clustering, a partioning clustering, a density-based clustering, a model-based clustering, a grid-based clustering, a soft-computing clustering. The hierarchical clustering may include an agglomerative hierarchical clustering and a divisive hierarchical clustering, a single-link clustering, a complete-link clustering, an average-link clustering, etc. The partioning clustering may include an error minimum algorithm (for example, a K-means algorithm, a K-medoids method, a K-prototypes algorithm), a graph-theoretic clustering, etc. The density-based method may include an expectation maximization algorithm, a density-based spatial clustering of applications with noise (DB-SCAN) algorithm, an ordering points to identify the clustering structures (OPTICS) algorithm, an AutoClass algorithm, a selection of negatives through observed bias (SNOB) algorithm, a MCLUST algorithm, etc. The model-based clustering may include a decision tree clustering, a neural network clustering, a self-organizing map clustering, etc. The soft-computing clustering may include a fuzzy clustering, an evolutionary approaches for clustering, a simulated annealing for clustering, etc. In some embodiments, the classification of a user may be adjusted in a self-adaptive way or manually to control the number of classes and/or the size (population) of one or more classes. In some embodiments, one class may include multiple individual users. In some embodiments, one class may include one individual user. The classes may be dynamically evolved or updated by processor 202 when data relating to an image, a user, and/or a patient is fed into the processor 202. In some embodiments, new classes may be created by processor 202 when one or more users may not be categorized into the existing classes.

At 303, processor 202 may process the image and/or improve user experience based on the obtained data and model. Merely by way of example, processing the image may include image segmentation, image enhancement, image fusion, image compression, or the like, or any combination thereof. Improving the user experience may include adjusting the user interface, adjusting the workflow, etc. In some embodiments, adjusting the user interface may include customizing the user interface according to the user or a class to which the user belongs. In some embodiments, adjusting the workflow may include customizing the workflow according to the user or a class to which the user belongs.

In some embodiments, processor 202 may process the image and/or improve user experience according to the profile of the user, a class to which the user belongs, one or more user in the class that the user belongs, or the like, or the combination thereof.

In some embodiments, processor 202 may perform one or more steps in process 300 (e.g., obtaining a model, segmenting an image, enhancing an image, adjusting the user interface, adjusting the workflow, etc.) during the down-time of scanner 101. Alternatively or additionally, processor 202 may perform one or more steps in process 300 during the work-time of scanner 101.

Obtaining a Model for Image Segmentation

Figure 4:
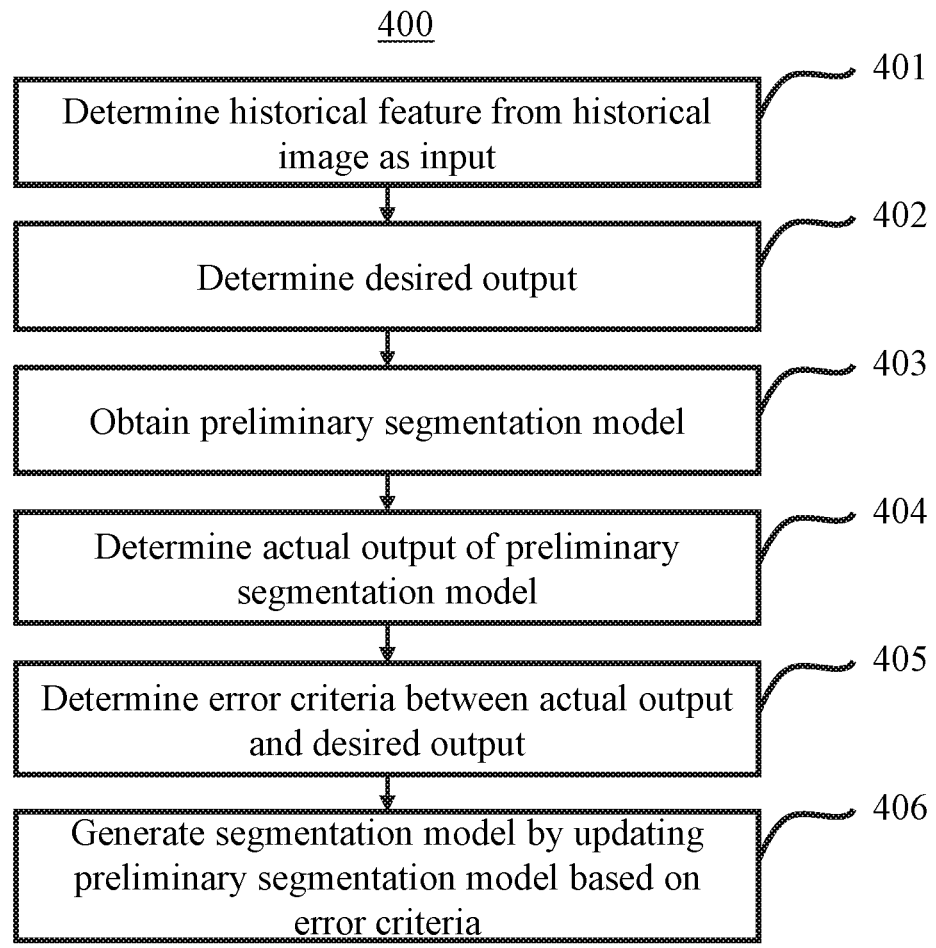
FIG. 4 is a flowchart of an exemplary process of obtaining a segmentation model according to some embodiments.

FIG. 4 is a flowchart of an exemplary process 400 of obtaining a segmentation model, which may be used in step 302 of process 300 illustrated in FIG. 3, according to some embodiments.

At 401, processor 202 may determine one or more historical features from one or more historical images as inputs for a segmentation model (a new model or a previously generated model). In some embodiments, the image(s) may be previously acquired image(s) (e.g., the image(s) acquired from scanner 101, computing device 102 and/or server 104). In some embodiments, processor 202 may determine one or more historical spatial features from the image(s). The spatial feature(s) may be relating to the overall or local pixel intensities (overall or local brightness), a location of an object (e.g., a tissue, an organ, a lesion, blood flow, etc.), a length or size of an object (e.g., a tissue, an organ, a lesion, blood flow, etc.), etc. in an image. For example, the spatial feature(s) identified may include an area of an object, an orientation of an object, a shape of an object, an overall or local brightness, a location of an object, a boundary of an object, an edge of an object, a corner of an object, a ridge of an object, a speckle content, an overall or local gradient, a flow velocity, a flow power, or the like, or any combination thereof. In some embodiments, processor 202 may determine one or more historical temporal features from two or more images. The historical temporal features may relate to changes or variations in certain physical quantities in a plurality of images or an image sequence consisting of two more images. For example, the historical temporal features may include a time pattern, a motion, a temporal gradient, or the like, or any combination thereof. For example, processor 202 may determine the motion based on time sequences analysis of the historical features. The time sequences analysis of the historical features may include the analysis of the images over a certain time period. The analysis of the images over time may reveal a pattern of the motion existing in multiple static images captured over time. The motion may include heartbeat, contraction of blood vessel, etc. The pattern of motion may indicate a seasonality or periodicity that repeats itself. In some embodiments, moving averages or regression analysis may be used. Further, the analysis may employ certain type of filter (e.g., a morphological filter, a Gaussian filter, an unsharp filter, a frequency filter, a mean filter, a median filter, etc.) to the image data to dampen error. The analysis may be conducted in the time domain or in the frequency domain.

In some embodiments, processor 202 may process the image to determine feature(s) as one or more orthogonal inputs using a certain method. In some embodiments, the method may include a principal component analysis (PCA), an independent component analysis, an orthogonal decomposition, a singular value decomposition, a whitening method, or a sphering method, etc. The orthogonal inputs may be linearly unrelated.

At 402, processor 202 may determine a desired output. In some embodiments, the desired output may be manually determined or designated by a user, or automatically determined by processor 202 based on the previous results of segmentation. In some embodiments, the desired output may include a tissue type (to be identified), an image view, one or more imaging parameters, an anatomy, or the like, or any combination thereof. Exemplary imaging parameter(s) may include saturation, contrast (global or local), sharpness, brightness, dynamic range, spatial filter, persistence, or the like, or any combination thereof.

For illustration purpose only, the inputs and the desired output of a segmentation model for determining 4 chambers of a heart are described. The inputs to the model to determine the chambers of the heart may include boundary pixels (e.g., spatial locations normalized to the imaging depth and imaging width) whose spatial gradient exceeds a threshold, an evolution of the boundary pixels in time (e.g., one or more motion vectors corresponding to the spatial changes in pixel position of the boundary point over time), an area computed from a rough contour of the identified boundary, a change of an area over time, a multi-modal relevant input, beam-formed radio frequency (RF) data, channel data, a signal with an in-phase component and a component that is in quadrature (e.g., IQ data), or the like, or any combination thereof. In some embodiments, the multi-modal relevant input may be a Color Doppler data, including, for example, a location of the Color Doppler boundaries (relative to the B-mode boundaries), an area of the color pixels, etc. In some embodiments, the phase of the RF data may indicate signal information. For example, a stationary phase of the RF data may indicate a main-lobe signal, a linear trended phase of RF data may indicate a grating-lobe signal, and a random phase of RF phase may indicate a clutter signal.

The desired output of the model may include an anatomy (e.g., a heart, a breast, an abdomen, etc.), an imaged view (e.g., a 4-chamber view, a 2-chamber view, a parasternal long axis (PLAX) view, an aortic outflow view, a suprasternal view, a sub-costal view, etc.), a desired imaging parameter range (e.g., a dynamic range, a spatial filter, an edge enhancement, a contrast enhancement, an imaging frequency, a line density, etc.), or the like, or any combination thereof.

Referring to FIG. 4, at 403, processor 202 may obtain a preliminary segmentation model (a new model or a previously generated model). In some embodiments, processor 202 may initialize the preliminary segmentation model (the new model). For example, processor 202 may initialize the preliminary segmentation model by randomly setting weights (or coefficients) of one or more nodes in the preliminary segmentation model. In some embodiments, processor 202 may update the preliminary segmentation model (the previously generated model). For example, the weights of one or more nodes in the preliminary segmentation model may be updated according to the identified inputs (e.g., historical spatial features and/or historical temporal features from an image, etc.) and the identified desired outputs (e.g., the tissue type, the image view, one or more imaging parameters, the anatomy, etc.) as training sets.

In some embodiments, the training set may be a set of data used for training the preliminary segmentation model or the models for segmenting images. The training set may include one or more historical segmented images that are generated based on historical images. In some embodiments, a training set obtaining module (not shown) may automatically determine one or more training sets based on one or more historical images. For example, processor 202 may generate one or more historical segmented images by automatically segmenting one or more historical images. In some embodiments, processor 202 may also determine the input and desired output of the preliminary segmentation model based on the training sets and the historical images.

At 404, processor 202 may determine an actual output of the preliminary segmentation model. In some embodiments, the actual output may be mapped with the inputs by the preliminary segmentation model. The preliminary segmentation model may include two or more layers of weights. Merely by way of example, the preliminary segmentation model includes two layers of weights. The first layer of weights may convert the inputs to an intermediate by summing the products of the weights with inputs. The intermediate may be passed to the second layer of weights. The second layer of weights may convert the intermediate to an actual output by summing the products of the weights with the intermediate. In some embodiments, the input, intermediate, and actual output may be multidimensional. For illustration purpose only, the actual output of the preliminary segmentation model for determining the 4 chambers of the heart may be a segmented heart with a size larger than that of the desired segments (i.e., four segments representing the four chambers).

At 405, processor 202 may determine an error criteria between the desired output and the actual output(s) of the preliminary segmentation model determined at 404. In some embodiments, the error criteria may be manually determined or designated by a user, or automatically determined by processor 202 based on the previous result of segmentation. In some embodiments, the error criteria may be determined by subtracting the actual output from the desired output. For example, the error criteria between the actual 4-chamber view and the desired 4-chamber view may be the difference in size or boundaries. In some embodiments, the error criteria may be a minimum error criteria.

At 406, processor 202 may generate a segmentation model by modifying the preliminary segmentation model based on the determined error criteria between the desired output and the actual output(s). For example, processor 202 may generate the segmentation model by evolving (or updating) one or more coefficients and/or weights of one or more nodes in the preliminary segmentation model based on the error criteria (e.g., the size difference in 4-chamber view). The evolving of coefficients and/or weights may be achieved by implementing an optimization algorithm, such as, a random search, a Newton's method, a Quasi-Newton method, an evolutional algorithm, a coordinate descent method, a proximal gradient method, a gradient descent method, a steepest descent method, a conjugate gradient method, a bi-conjugate gradient method, etc.

In some embodiments, the error criteria may be determined by processor 202 according to following steps. Processor 202 may obtain a plurality of preliminary models. The preliminary models may be segmentation models segmenting an image into one or more segments. The preliminary models may be system-default models, user-predefined models, or any other existing models. Processor 202 may generate a plurality of preliminary images according to the plurality of preliminary models and the received data relating to the image. For example, processor 202 may apply the plurality of preliminary models to the received data and generate the preliminary images. The preliminary images may be segmented images. For example, each preliminary image may include one or more segments. Processor 202 may identify or receive a desired output including a selection, by the user, of an image from the plurality of preliminary images. Processor 202 may determine the error criteria based on the plurality of preliminary models and the selected image from the plurality of preliminary images.

In some embodiments, processor 202 may loop one or more steps (e.g., processor 202 may loop steps of 403-406 after step 406 of a last process 400) to obtain a model. In some embodiments, processor 202 may implement one or more steps in process 400 consecutively, or in parallel, or in any other orders. In some embodiments, processor 202 may obtain the segmentation model based on the circumstance of the image under which the image is acquired or captured, including, for example, the imaging mode, the anatomy, the preset used, the imaged view, the range of imaging parameter(s), or the like, or any combination thereof. In some embodiments, processor 202 may end the iteration when the error criteria between actual output and desired output is below a predetermined threshold. In some embodiments, the threshold may be adjusted or determined according to the imaging conditions, physical scenarios in which the image is acquired, user preference, or any other requirements.

Obtaining a Model for Image Enhancement

Figure 5:
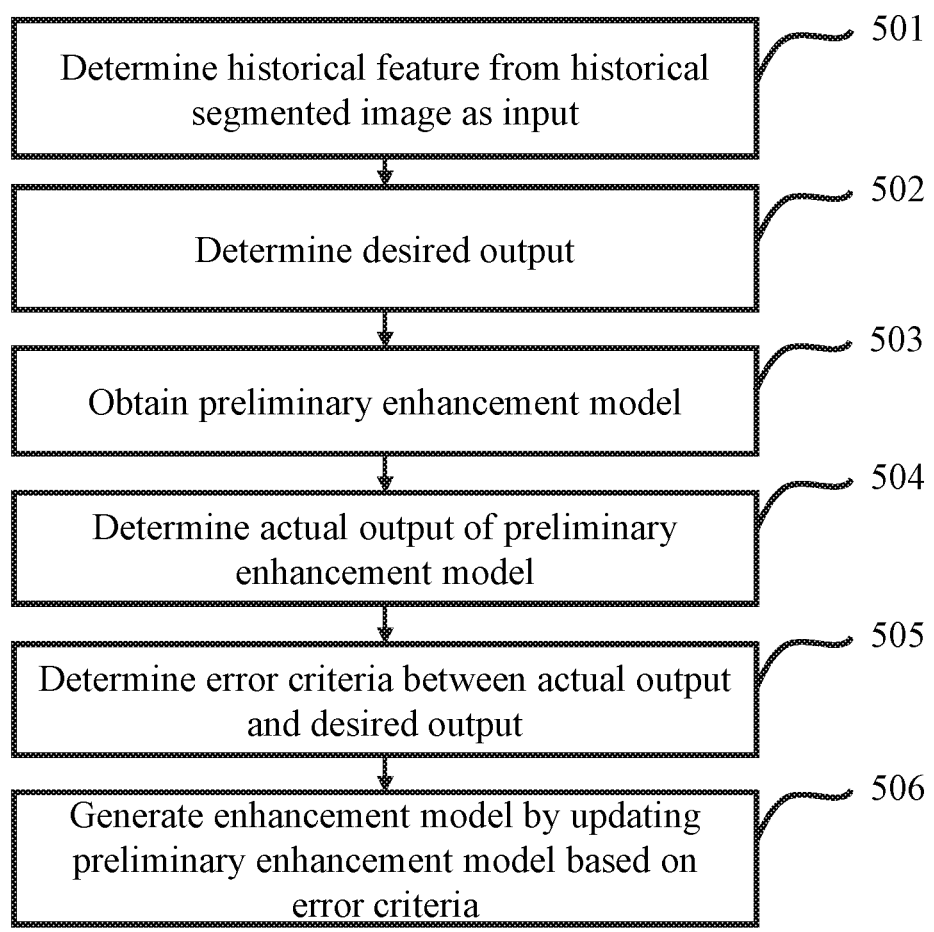
FIG. 5 is a flowchart of an exemplary process of obtaining an enhancement model according to some embodiments.

FIG. 5 is a flowchart of an exemplary process 500 of obtaining an enhancement model for image enhancement, which may be used in step 302 of process 300 illustrated in FIG. 3, according to some embodiments. At 501, processor 202 may determine one or more historical features from historical segmented images as inputs for a model (a new model or a previously generated model). In some embodiments, the feature(s) may include a size of a segment, an area of a segment, a location (a spatial location, or a relative location to a reference point or object) of a segment, a local or overall brightness, a speckle content, or the like, or any combination thereof. In some embodiments, the segmented image(s) may be acquired from the process and/or method in step 803 of process 800 illustrated in FIG. 8 in the present disclosure. In some embodiments, the segmented image(s) may be historical segmented images stored in device 200.

In some embodiments, processor 202 may perform image enhancement, imaging parameter identification, and non-imaging aspects using the identified feature(s) from the segmented image. Merely by way of example, the non-imaging aspects may include an anatomy identification, a workflow enhancement, etc. Exemplary workflow enhancement may include an automated filling-in a data field, an automated identification of a region of interest, etc. For example, the region of interest in a Color Doppler may include a position of an object, a size of an object, a steer of a beam/a color box/a probe positioning, etc. As another example, the region of interest in a PW Doppler may include a gate size of the pulse, a position of an object, a steer of a PW Doppler angle, etc.

At 502, processor 202 may determine a desired output. In some embodiments, the desired output may be manually determined by a user, or automatically determined by processor 202 based on the previous processes. In some embodiments, the desired output of an image enhancement may be the processed image(s) that are more suitable for display and/or further image analysis.

In some embodiments, the desired output may be manually determined or designated by the user, or automatically determined by processor 202 based on the previous results of image enhancements. Merely by way of example, the desired output may include a contrast (local or global), a brightness (local or global), a saturation (local or global), a sharpness (local or global), a grayscale of the image, or the like, or any combination thereof.

At 503, processor 202 may obtain an enhancement model. In some embodiments, processor 202 may initialize an enhancement model (a new model). For example, processor 202 may initialize the enhancement model by randomly setting coefficients and/or weights of one or more modes in the enhancement model. In some embodiments, processor 202 may update an enhancement model (a previously generated model). For example, processor 202 may adjust the coefficients and/or weights of one or more nodes in the enhancement model based on the identified inputs (e.g., the size/area/location of the segment, the local or overall brightness, the speckle content, etc.) and identified desired outputs (e.g., the local or global contrast/brightness/saturation/sharpness, the grayscale of the image, etc.) as training sets after the initialization.

In some embodiments, the training set may be a set of data used for training the preliminary enhancement model or the models for enhancing the images. In some embodiments, the training set obtaining module (not shown) may automatically determine one or more training sets based on the one or more historical segmented images. For example, processor 202 may determine one or more values of one or more imaging parameters by automatically enhancing one or more historical segmented images. In some embodiments, processor 202 may also determine the input and desired output of the preliminary enhancement model based on the training sets and the historical segmented images.

At 504, processor 202 may determine an actual output of the preliminary enhancement model based on the input. In some embodiments, the actual output may be mapped with the inputs by the preliminary enhancement model. The preliminary enhancement model may include two or more layers of weights. Merely by way of example, the preliminary enhancement model includes two layers of weights. The first layer of weights may convert the inputs to an intermediate by summing the products of the weights with inputs. The intermediate may be passed to the second layer of weights. The second layer of weights may convert the intermediate to an actual output by summing the products of the weights with the intermediate. In some embodiments, the input, intermediate, and actual output may be multidimensional. For example, the actual output of the enhancement model for determining the 4-chamber of the heart may be a 4-chamber view with a contrast lower than that of the desired 4-chamber view (e.g., 4 segments representing the four chambers).

At 505, processor 202 may determine an error criteria between the desired output and the actual output(s) of the preliminary enhancement model determined at 504. In some embodiments, the error criteria may be manually determined or designated by a user, or automatically determined by processor 202 based on the previous result of enhancement. In some embodiments, the error criteria may be determined by subtracting the actual output from the desired output. For example, the error criteria between the actual 4-chamber view and the desired 4-chamber view may be the difference in contrast.

At 506, processor 202 may generate an enhancement model by modifying the preliminary enhancement model based on the determined error criteria between the desire output and the actual output. For example, processor 202 may train the preliminary enhancement model by evolving (or updating) one or more coefficients and/or weights of one or more nodes in the model based on the error criteria (e.g., the contrast difference in the 4-chamber view). The evolving of coefficients and/or weights may be achieved by implementing an optimization algorithm, such as, a random search, a Newton's method, a Quasi-Newton method, an evolutional algorithm, a coordinate descent method, a proximal gradient method, a gradient descent method, a steepest descent method, a conjugate gradient method, a bi-conjugate gradient method, etc.

In some embodiments, the error criteria may be determined by processor 202 according to following steps. Processor 202 may obtain a plurality of preliminary models. The preliminary models may be enhancement models enhancing an image and generating an enhanced image. The preliminary models may be system-default models, user-predefined models, or any other existing models. Processor 202 may generate a plurality of preliminary images according to the plurality of preliminary models and the received data relating to the image. For example, processor 202 may apply the plurality of preliminary models to the received data and generate the preliminary images. The preliminary images may be enhanced images. For example, each enhanced image may have one or more imaging parameters different from the original image. Processor 202 may identify or receive a desired output including a selection, by the user, of an image from the plurality of preliminary images. Processor 202 may determine the error criteria based on the plurality of preliminary models and the selected image from the plurality of preliminary images.

In some embodiments, processor 202 may loop one or more steps (e.g., processor 202 may loop steps of 503-506 after step 506 of a last process 500) to obtain a model. In some embodiments, processor 202 may implement one or more steps in process 500 consecutively, or in parallel, or in any other orders. In some embodiments, processor 202 may obtain the enhancement model based on the circumstance of the image under which the image is acquired or captured, including, for example, the imaging mode, the anatomy, the preset used, the imaged view, the imaging parameter range, or the like, or any combination thereof. In some embodiments, processor 202 may end the iteration when the error criteria between actual output and desired output is below a predetermined threshold. In some embodiments, the threshold may be adjusted or determined according to the imaging conditions, physical scenarios in which the image is acquired, user preference, or any other requirements.

Obtaining a Model in User Interface

Figure 6:
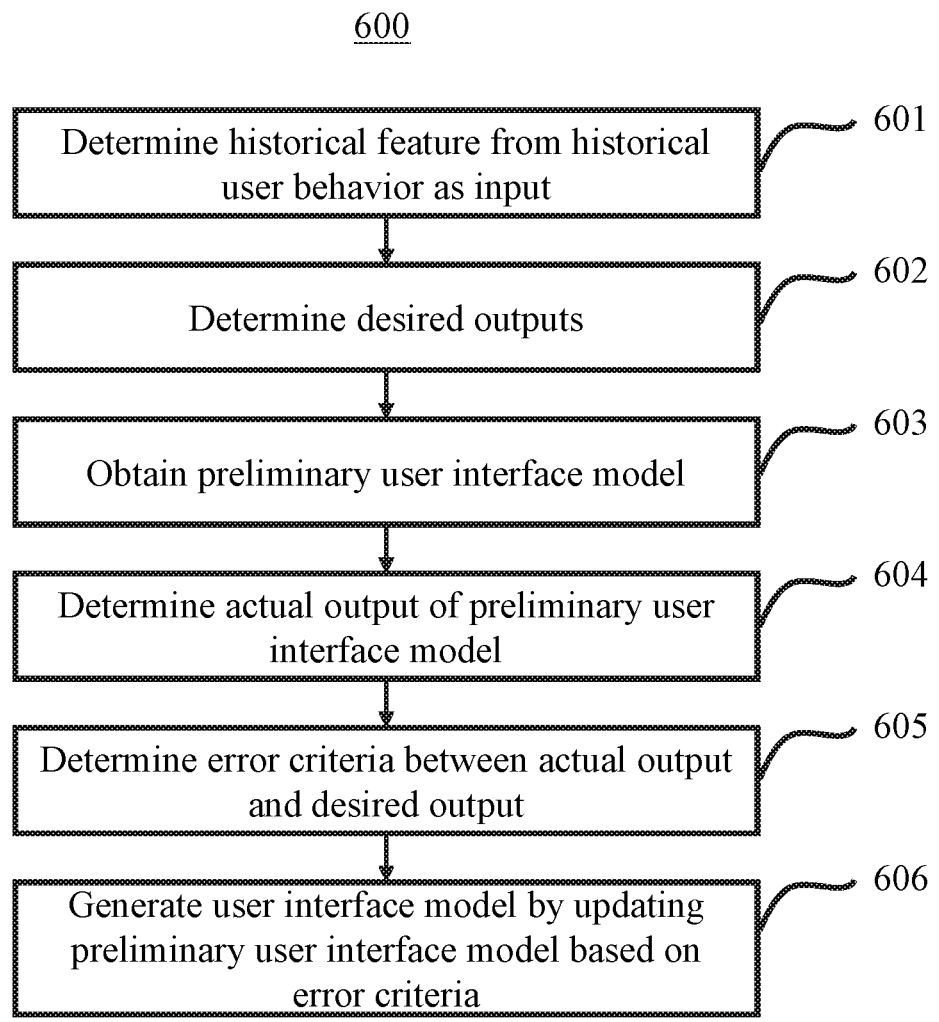
FIG. 6 is a flowchart of an exemplary process of obtaining a user interface model according to some embodiments.

FIG. 6 is a flowchart of an exemplary process 600 of obtaining a user interface model, which may be used in step 302 of process 300 illustrated in FIG. 3, according to some embodiments.

At 601, processor 202 may determine one or more historical features from one or more historical patterns of user behavior(s) as inputs for a model (a new model or a previously generated model). In some embodiments, the patterns of user behavior may be retrieved from previously acquired interaction(s) between the user and one or more components of system 100 through the user interface thereof (e.g., the interaction(s) acquired from scanner 101, computing device 102, and/or server 104 through the user interface thereof). In some embodiments, the patterns of user behavior may include context data associated with a time of an examination of a patient, a location of the examination, a user (i.e., a physician or hospital personnel), a patient, an environment condition, an examination type, or the like, or any combination thereof. Features may include, soft keys (or folders of soft keys) displayed on a screen, relative positions of soft keys (or folders of soft keys) on the screen, frequencies of soft keys being pressed, grouping of folders of soft keys, tools, wizards, or information panels on the screen, relative positions of tools, wizards, or information panels on the screen, or the like, or the combination thereof. Merely by way of example, the user behavior may include rotating/transforming/moving/scaling an image acquired, selecting/activating/deactivating a function, selecting a button, pressing a widget (e.g., a finish widget, an exit widget, an additional widget, etc.), performing a particular gesture, exiting a selected function, deactivating a widget, closing a window, opening a window, invoking a measurement report or a review screen, or the like, or any combination thereof. In some embodiments, processor 202 may track the user's interactions with one or more components of system 100 (e.g., scanner 101, computing device 102, and/or server 104). For example, processor 202 may track the path of the user's mouse pointer and the buttons (or links) that the user clicks over time, etc.

In some embodiments, processor 202 may determine a class of a user interface based on one or more features of the user interface, including, soft keys (or folders of soft keys) displayed on a screen, relative positions of soft keys (or folders of soft keys) on the screen, frequencies of soft keys being pressed, grouping of folders of soft keys, tools, wizards, or information panels on the screen, relative positions of tools, wizards, or information panels on the screen, or the like, or the combination thereof.

At 602, processor 202 may determine a desired output. In some embodiments, the desired output may be manually determined or designated by a user, or automatically determined by processor 202 based on the previous data relating to the interactions between the user and one or more components of system 100. In some embodiments, the desired output may be a preferred user setting for the user interface of one or more components of system 100 (scanner 101, computing device 102, and/or server 104) including, for example, a desire function to be performed on the image(s) acquired, a location of a user control, the number of user controls, an interface for waveform graphics (e.g., a waveform tracing, etc.), or the like, or any combination thereof. Exemplary desire function may include an examination type (e.g., a continue wave Doppler, a Power Doppler, a C-mode Doppler, a B-mode Doppler, a multi-modal ultrasound, etc.), an automated measurement, an automated image segmentation, an automated image enhancement, an automated calculation, or the like, or any combination thereof. In some embodiments, the desired output may be determined at least based on the user's input. For example, the user may designate the number and/or locations of icons representing different functions by configuring a layout of the user interface.

At 603, processor 202 may obtain a user interface model. In some embodiments, processor 202 may initialize the user interface model (a new model). For example, processor 202 may initialize the user interface model by randomly setting coefficients and/or weights of one or more nodes in the user interface model.

In some embodiments, processor 202 may update a user interface model (a previously generated model). For example, processor 202 may adjust the coefficients and/or weights of one or more nodes in the user interface model based on the identified inputs (e.g., one or more user behavior patterns) and identified desired outputs (e.g., a desire function, a location of a user control, the number of user controls, an interface for waveform graphics, etc.) as training sets.

In some embodiments, the training set may be a set of data used for training the preliminary user interface model or the model for adjusting the user interface. The training set may include one or more historical user interfaces that are collected from historical user behaviors. In some embodiments, the training set obtaining module (not shown) may automatically determine one or more training sets based on one or more historical user behaviors. For example, processor 202 may generate one or more historical user interface by automatically adjusting one or more historical user behaviors. In some embodiments, processor 202 may also determine the input and desired output of the preliminary user interface model based on the training sets and historical user behaviors.

At 604, processor 202 may determine an actual output of the preliminary user interface model. In some embodiments, the actual output may be mapped with the inputs by the preliminary user interface model. The preliminary user interface model may include two or more layers of weights. Merely by way of example, the preliminary user interface model includes two layers of weights. The first layer of weights may convert the inputs to an intermediate by summing the products of the weights with inputs. The intermediate may be passed to the second layer of weights. The second layer of weights may convert the intermediate to an actual output by summing the products of the weights with the intermediate. In some embodiments, the input, intermediate, and actual output may be multidimensional. For example, the actual output of the user interface model may be 5 user controls (while the desired output of the user interface model may be 6 user controls).

At 605, processor 202 may determine an error criteria between the desired output and the actual output(s) of the preliminary user interface model determined at 604. In some embodiments, the error criteria may be manually determined or designated by a user, or automatically determined by processor 202 based on the previous user interface. In some embodiments, the error criteria may be determined by subtracting the actual output from the desired output. For example, the error criteria between the number of actual user controls (e.g., 5 control buttons shown in the UI) and the number of desired user controls (e.g., 6 control buttons shown in the UI) may be the difference between the actual UI and desired UI (i.e., the extra control button shown in the desired UI using the above examples). As another example, the error criteria between the actual user control and the desired user control may be the difference of the control content. In some embodiments, the error criteria may be a minimum error criteria.

At 606, processor 202 may generate a user interface model by modifying the preliminary user interface model based on the error criteria (e.g., the difference in the number of user controls, the different content of user control, etc.). For example, processor 202 may train the preliminary user interface model by evolving (or adjusting) one or more coefficients and/or weights of one or more nodes in the user interface model based on the error criteria. The evolution of coefficients and/or weights may be achieved by implementing an optimization algorithm, such as, a random search, a Newton's method, a Quasi-Newton method, an evolutional algorithm, a coordinate descent method, a proximal gradient method, a gradient descent method, a steepest descent method, a conjugate gradient method, a bi-conjugate gradient method, etc.

In some embodiments, prior to 601, processor 202 may determine protocols and event sequences from previous studies based on historical data relating to the user. In some embodiments, the user behavior in step 601 may be identified from the event sequences and used for updating the user interface model. In some embodiments, an examination, a patient, and one or more patterns of user behavior may be manually identified prior to 601. In some embodiments, the protocols may include a measurement menu, an imaging condition (e.g., initializing a Doppler), a populating of a data field, an annotation of the image, or the like, or any combination thereof.

For illustration purpose only, an exemplary event sequence is described as follows. When viewing a left ventricular (LV) chamber, user A may perform an event sequence including the following events in order: determining a LV view; detecting and tracing a border; adjusting a cursor of the border lines; calculating one or more dimensions (e.g., volume, size, distance between specified points, etc.); plotting calculated parameters as a function of a cardiac cycle; displaying one or more important parameter ratios over a cardiac phase (e.g., the ration of systolic value to diastolic value, ejection fraction, etc.), etc. As another example, User B may perform an event sequence including the following events in order: determining a LV chamber; activating a color Doppler view; placing the cursor near a mitral value, or any other points of interest; activating a PW Doppler view to display spectral and/or velocity information; displaying one or more important parameter ratios over a cardiac phase (e.g., ejection fraction, etc.), etc.

In some embodiments, processor 202 may loop one or more steps (e.g., processor 202 may loop steps of 603-606 after step 606 of a last process 600) in process 600 to obtain a model. In some embodiments, processor 202 may implement one or more steps in process 600 consecutively, or in parallel, or in any other orders. In some embodiments, processor 202 may end the iteration when the error criteria between actual output and desired output is below a predetermined threshold. In some embodiments, the threshold may be adjusted or determined according to the specific application, physical scenarios in which the image is acquired, user preferences, or any other needs.

Obtaining a Model in Workflow

Figure 7:
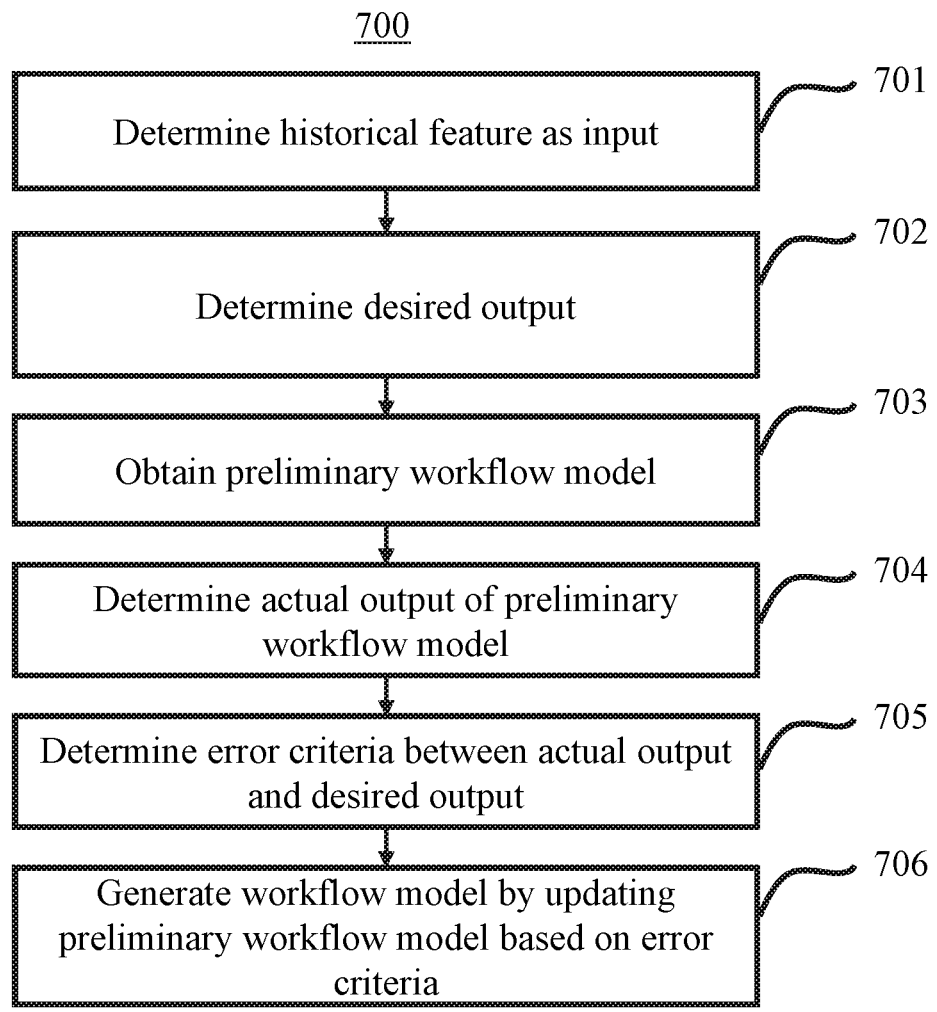
FIG. 7 is a flowchart of an exemplary process of obtaining a workflow model according to some embodiments.

FIG. 7 is a flowchart of an exemplary process 700 of obtaining a workflow model, which may be used in step 302 of process 300 illustrated in FIG. 3, according to some embodiments. At 701, processor 202 may determine one or more historical features as inputs for a model (a new model or a previously generated model). In some embodiments, the feature(s) may include feature(s) in functions of the workflow, feature(s) in user's usage pattern, or the like, or any combination thereof. Feature(s) in functions of the workflow may include an underlying anatomy of an object, a preset of a user or one or more components of system 100 relating to the workflow, a trace and/or waveform of a border, an annotation of an image, a protocol of an examination, the number of key presses for a given task, or the like, or any combination thereof. Features in user's usage pattern may include an invocation of key steps, a relative sequence of key steps, a repetition of key steps, a duration of time for one or more key steps, or the like, or any combination thereof. A key step may be important or crucial in a workflow. A key step may be classified or defined according to the workflow, for example, a cardiological workflow, an intestinal workflow, etc. In some embodiments, the key step may be classified or defined according to an individual user, a class or group of users. The key step for a user in a workflow may be configured manually or adapted automatically according to a class or group of users. In some embodiments, processor 202 may determine a class of a user based on one or more features determined as described above.

At 702, processor 202 may determine one or more desired outputs. In some embodiments, the desired output may be manually determined or designated by the user, or automatically determined by processor 202 based on the previous workflow(s) relating to the user. In some embodiments, the desired output may include an automated registration of traces with underlying waveforms, an automated suggestion of the intended trace and/or measurement, an automated filling-in of a text field, a frequency of a correction of a suggested workflow change, or the like, or any combination thereof.

At 703, processor 202 may obtain a workflow model. In some embodiments, processor 202 may initialize a workflow model (a new model). For example, processor 202 may initialize the workflow model by randomly setting coefficients and/or weights of one or more nodes in the workflow model. In some embodiments, processor 202 may update a workflow model (a previously generated model). For example, processor 202 may adjust the coefficients and/or weights of one or more nodes in the workflow model based on the identified inputs (e.g., the underlying anatomy, the preset, the trace, the annotation, etc.) and identified desired outputs (the automated registration of traces with underlying waveforms, the automated suggestion of the intended trace and/or measurement, the automated filling-in of a text field, the frequency of the correction of the suggested change, etc.) as training sets.

In some embodiments, the training set may be a set of data used for training the preliminary workflow model or the model for adjusting the workflow. The training set may include one or more historical workflows identified based on the historical user behavior. In some embodiments, the training set obtaining module (not shown) may automatically determine one or more training sets based on one or more historical workflows. For example, processor 202 may generate one or more historical workflows by automatically adjusting one or more historical workflows. In some embodiments, processor 202 may also determine the input and desired output of the preliminary workflow model based on the training sets and the historical workflows.

At 704, processor 202 may determine an actual output of the preliminary workflow model. In some embodiments, the actual output may be mapped with the inputs by the preliminary workflow model. The preliminary workflow model may include two or more layers of weights. Merely by way of example, the preliminary workflow model includes two layers of weights. The first layer of weights may convert the inputs to an intermediate by summing the products of the weights with inputs. The intermediate may be passed to the second layer of weights. The second layer of weights may convert the intermediate to an actual output by summing the products of the weights with the intermediate. In some embodiments, the input, intermediate, and actual output may be multidimensional. For example, the actual output of the workflow model may be an automated filling-in of a text field with the words of "automated filling-in the text field" (while the desired output of the workflow model may be the words of "automated filling-in the menu box").

At 705, processor 202 may determine an error criteria between the desired output and the actual output(s) of the preliminary workflow model determined at 704. In some embodiments, the error criteria may be manually determined or designated by a user, or automatically determined by processor 202 based on the previous result of workflow. In some embodiments, the error criteria may be a minimum error criteria. In some embodiments, the error criteria may be determined by subtracting the actual output from the desired output. For example, the error criteria between the actual automated filling-in of the text field and the desired automated filling-in of the text field may be the difference of filled filling words.

At 706, processor 202 may generate a workflow model by modifying the preliminary workflow model based on the error criteria. For example, processor 202 may train the workflow model by evolving (or adjusting) one or more coefficients and/or weights of one or more nodes in the workflow model based on the error criteria (e.g., the difference between the automated filled filling words by the desired output and the actual output). The evolution of coefficients and/or weights may be achieved by implementing an optimization algorithm, such as, a random search, a Newton's method, a Quasi-Newton method, an evolutional algorithm, a coordinate descent method, a proximal gradient method, a gradient descent method, a steepest descent method, a conjugate gradient method, a bi-conjugate gradient method, etc.

In some embodiments, processor 202 may loop one or more steps in process 700 to obtain a model. In some embodiments, processor 202 may implement one or more steps in process 700 consecutively, or in parallel, or in any other orders. In some embodiments, processor 202 may end the iteration when the error criteria between actual output and desired output is below a predetermined threshold. In some embodiments, the threshold may be adjusted or determined according to the application, user preference, or any other requirements.

Application of the Model for Image Segmentation

Figure 8:
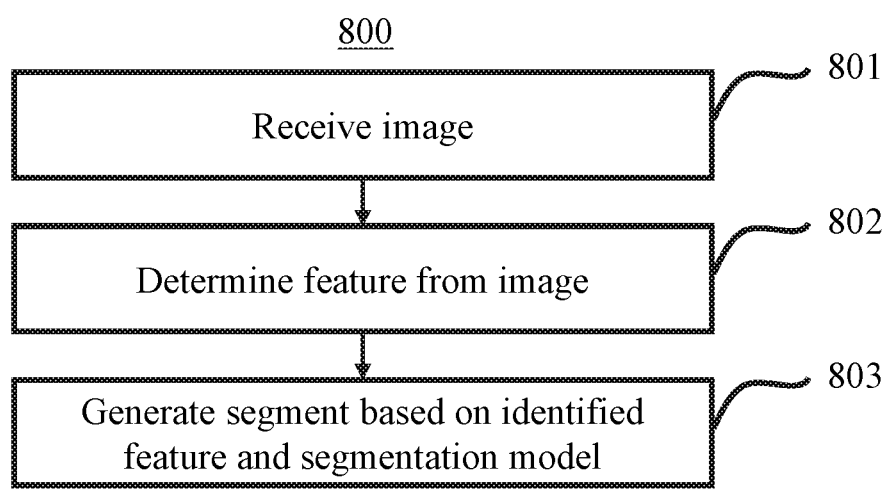
FIG. 8 is a flowchart of an exemplary process of using the model in segmentation according to some embodiments.

FIG. 8 is a flowchart of an exemplary process 800 of using the model in segmentation, which may be used in step 303 of process 300 illustrated in FIG. 3, according to some embodiments. At 801, processor 202 may receive an image. In some embodiments, the image may be acquired from scanner 101. In some embodiments, the image may be a pre-processed image stored in system 100 (i.e., computing device 102 and/or server 104).

At 802, processor 202 may determine one or more features from the image identified at 801. In some embodiments, the feature(s) may include an area of an object, an orientation of an object, a shape of an object, an overall or local brightness, a location of an object, a boundary of an object, a speckle content, an overall or local gradient, a flow velocity, a flow power, a time pattern, a motion, a temporal gradient, or the like, or any combination thereof.

At 803, processor 202 may generate segments based on the identified features and the segmentation model. In some embodiments, different segments may be generated for different tissues, organs, muscles, membranes, bones, chambers, etc. In some embodiments, the process and method of identifying features and/or generating segments may be described in one or more steps of process 1000 illustrated in FIG. 10 in the present disclosure.

In some embodiments, processor 202 may loop one or more steps in process 800 (e.g., step 802 and/or step 803) to obtain a model. In some embodiments, processor 202 may implement one or more steps in process 800 consecutively, or in parallel, or in any other orders.

Application of the Model for Image Enhancement

Figure 9:
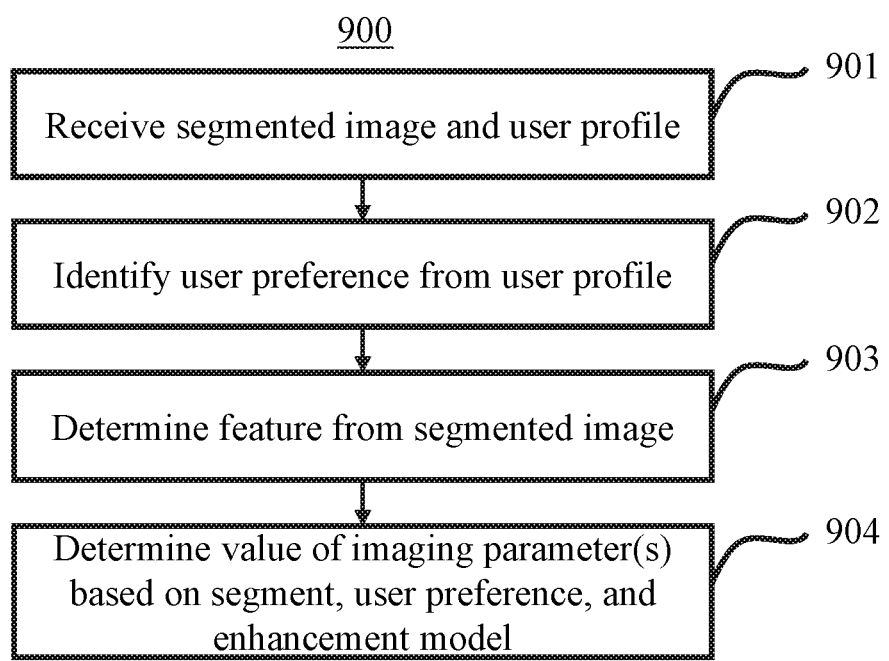
FIG. 9 is a flowchart of an exemplary process of using the model in enhancement according to some embodiments.

FIG. 9 is a flowchart of an exemplary process 900 of using the model for image enhancement, which may be used in step 303 of process 300 illustrated in FIG. 3, according to some embodiments. At 901, processor 202 may receive a segmented image and a user profile. In some embodiments, the user profile may include data associated with a user. Merely by way of example, the user profile may include the user's identity, the user's preferences, etc.

At 902, processor 202 may identify one or more user preferences from the user profile. In some embodiments, the user preference may include one or more imaging parameters in which the user may be interested, which may be determined according to the previous image enhancements. The imaging parameters may include, for example, the type of the examination, the imaging mode, the imaging view, the patient, or the like, or any combination thereof. At 903, processor 202 may determine one or more features from the segmented image. In some embodiments, the feature(s) may include a size of the segment, an area of the segment, a location (a spatial location, or a relative location to a reference point or object) of the segment, an orientation of a segment (a spatial orientation, or a relative orientation to a reference point or object), a local or overall brightness, a speckle content, or the like, or any combination thereof.

At 904, processor 202 may determine the value of the imaging parameter(s) based on the segment(s), and/or the user preference, and/or the enhancement model. In some embodiments, the imaging parameters may include a dynamic range, a spatial filter, a persistence, or the like, or any combination thereof. In some embodiments, different segments may share a common set of parameters. In some embodiments, different segments may be adjusted by different sets of parameters. In some embodiments, the value of the imaging parameters may be determined by steps 1007, 1013 and 1016 of process 1000 illustrated in FIG. 10 and described above.

In some embodiments, processor 202 may loop one or more steps in process 900 (e.g., steps 902, 903 and 904) to obtain a model. In some embodiments, processor 202 may implement one or more steps in process 900 consecutively, or in parallel, or in any other orders.

Figure 10:
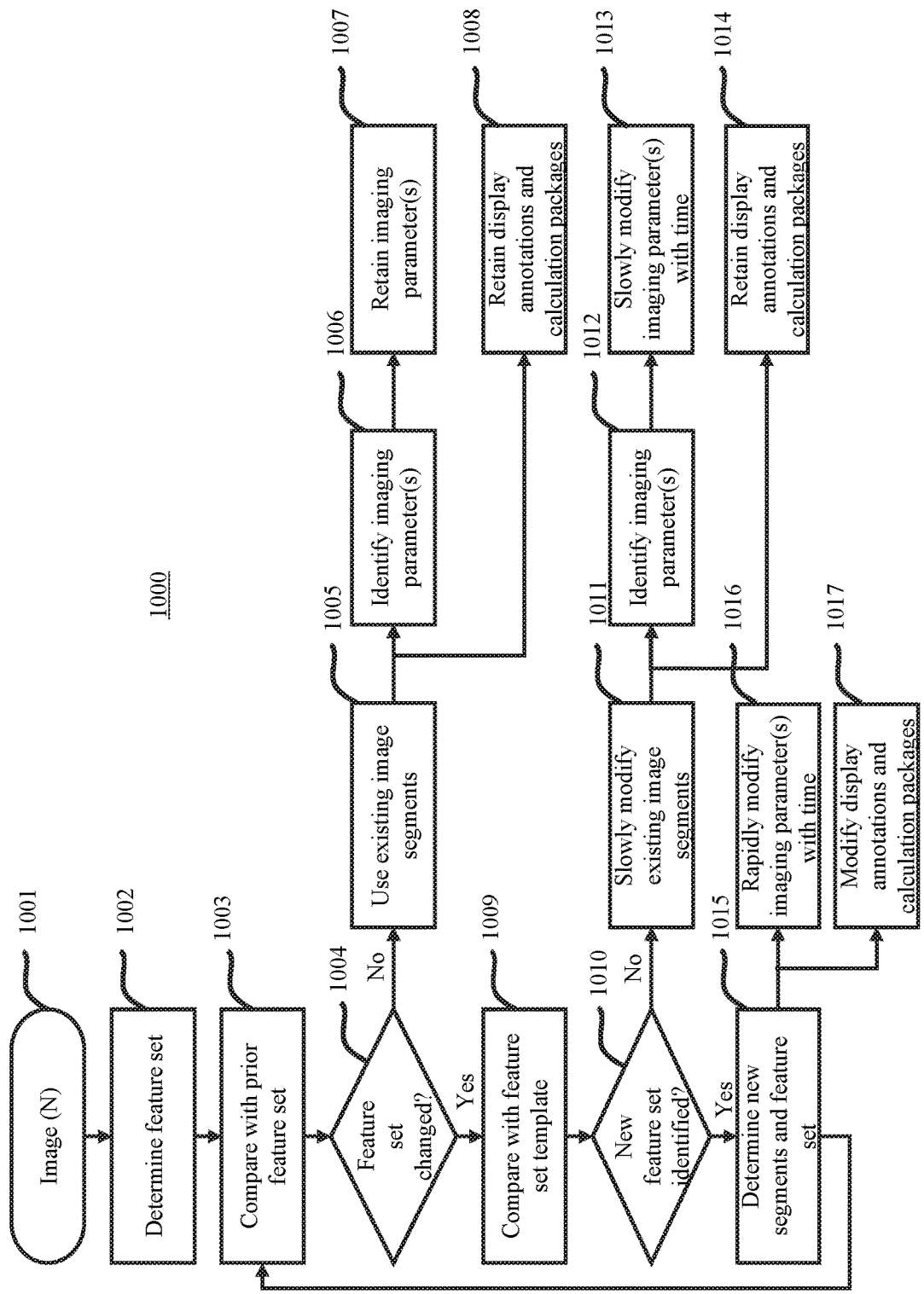
FIG. 10 is a flowchart of an exemplary process of image segmentation and enhancement according to some embodiments.

FIG. 10 is a flowchart of an exemplary process 1000 of image segmentation and enhancement, which may be used in step 803 of process 800 illustrated in FIG. 8 and/or step 904 of process 900 illustrated in FIG. 9, according to some embodiments. For illustration purpose only, an image segmentation process 1000 in an ultrasound imaging is described below for better understanding. In some embodiment, the ultrasound imaging may include an amplitude mode (A-mode) ultrasonography, a brightness mode (B-mode) ultrasonography, a motion mode (M-mode) ultrasonography, a Doppler mode ultrasonography, a pulse inversion mode ultrasonography, a harmonic mode ultrasonography, a contrast ultrasonography, a molecular ultrasonography, an ultrasound elasticity imaging, a compression ultrasonography, or the like, or any combination thereof. Exemplary Doppler mode ultrasonography may include a color Doppler mode (C-mode) ultrasonography, a continuous wave Doppler mode (CW-mode) ultrasonography, a pulse wave Doppler mode (PW-mode) ultrasonography, etc. In some embodiments, the mode of the ultrasound imaging described above may be used individually or combined as a multi-modal ultrasound. In some embodiments, the multi-modal information may be acquired in sequence. In some embodiments, the multi-modal information may be acquired simultaneously. Merely by way of example, the multi-modal ultrasound may include a combination of B-mode and C-mode, a combination of B-mode and CW-mode, a combination of B-mode, C-mode and PW-mode, etc.

At 1001, processor 202 may acquire one or more images. In some embodiments, the image(s) may be acquired from scanner 101, computing device 102 and/or server 104. For example, I/O 204 may receive the image(s) from scanner 101, and transmit the image(s) to processor 202 for image processing. In some embodiments, the image(s) may be stored in storage 203. For example, the image(s) may be pre-processed by processor 202 and store in storage 203 for segmentation.

In some embodiment, processor 202 may implement process 1000 using two or more image versions of an image. In some embodiments, the image versions may include a tissue version and a flow version of the image. For example, the tissue version of the image may include features, such as a tissue, a muscle, etc.; while the flow version may include features, such as a movement of blood, a pulsing of muscle(s), etc.

At 1002, processor 202 may determine one or more feature sets from the image acquired at 1001. In some embodiments, the feature set may include one or more image features. For example, the features may include a size of an object, a shape of an object, an area of an object, a local or overall brightness, a speckle content, a location (a spatial location, or a relative location to a reference point or object) of a segment, an orientation (a spatial orientation, or a relative orientation to a reference point or object), a local or overall gradient, a temporal pattern, a flow velocity, a flow power, or the like, or any combination thereof. In some embodiments, the feature set may include one or more temporal features relating to the image(s). For example, the features may include a relative temporal location of a segment.

In some embodiments, processor 202, at 1002, may determine different features in different modes of ultrasound imaging. Merely by way of example, processor 202 may determine a local or overall brightness, a speckle content, an area of an object, and/or a shape of an object as features in a B-mode ultrasound image segmentation. Alternatively or additionally, processor 202 may determine a size of an object, an orientation of an object, a local or overall gradient, a temporal pattern, a flow velocity, and/or a flow power as features in a C-mode ultrasound image segmentation. Alternatively or additionally, processor 202 may determine a local or overall gradient, a temporal pattern, a flow velocity, and/or a flow power as features in a PW-mode ultrasound image segmentation. Alternatively or additionally, processor 202 may determine a relative spatial location of an object, and a relative temporal location of the segment in a multi-modal ultrasound image segmentation.

At 1003, processor 202 may compare the extracted feature set with a prior feature set. The prior feature set may be a historical feature set determined from previous studies relating to the image segmentation and/or image enhancement. In some embodiments, the prior feature set may be stored in system 100 (e.g., computing device 102 and/or server 104). In some embodiments, processor 202 may use one or more algorithms, methods, processes, formulas, rules, or the like, to determine a degree of similarity between the extracted feature set and the prior feature set. Exemplary algorithms to determine the degree of similarity may include a key point matching, a histogram method, a decision tree method, a perceptual hash algorithm, a scale-invariant feature transform (SIFT) method, or the like, or any combination thereof. Merely by way of example, the degree of similarity may be a difference value between the feature sets represented by a percent value. For example, the difference between the extracted area feature and the prior area feature of a same segment may be within 15% of each other.

At 1004, processor 202 may determine whether the feature set has changed. In some embodiments, whether the feature set has changed may be determined based on the degree of similarity between the extracted feature set and the prior feature set. Merely by way of example, processor 202 may determine the feature set has not changed when the difference value between the feature sets is less than a threshold (e.g., 20%). For example, processor 202 may determine the area feature has not changed if the percent value is within 15%, which is less than the threshold of 20%. However, processor 202 may determine the area feature has changed if the percent value is more than 20%. Merely by way of example, the value of the threshold may be restricted to 15%, 10%, 8%, 5%, 3% or 1%, etc.

In some embodiments, the threshold of determining whether the feature set has changed may be configurable. In some embodiments, the threshold may be determined according to the ultrasound imaging mode, the type of feature set, the user, the patient, one or more components in computing system 100 (e.g., scanner 101, computing device 102, and server 104).

If the feature set has not changed, at 1005, processor 202 may use existing image segments to segment the image identified at 1001. The existing image segments may be historical segments of previous image segmentations and/or image enhancements. In some embodiments, the existing image segments may be stored in computing system 100 (e.g., computing device 102 and/or server 104). In some embodiments, the method for segmenting the image may include a wavelet transformation, a Gabor transform, a morphological image processing method, an image frequency domain processing method, a histogram-based method (e.g., color histogram-based method, intensity histogram-based method, edge histogram-based method, etc.), a compression-based method, a region-growing method, a partial differential equation-based method, a variational method, a graph partitioning method, a watershed transformation, a model-based segmentation method, a multi-scale segmentation, a triangulation method, a co-occurrence matrix method, an edge detection method, a threshold method, or the like, or any combination thereof.

At 1006, processor 202 may identify one or more imaging parameters based on the existing image segments. In some embodiments, the imaging parameter(s) identified may include a gain, a dynamic range, a persistence, a compounding, a spatial filter, or the like, or any combination thereof.

At 1007, processor 202 may retain the identified imaging parameters. At 1008, processor 202 may retain the display annotations and calculation packages. In some embodiments, the annotation displayed may refer to any labeling of structures on the image to assist interpretation. Merely by way of example, the annotation may include a plain text, a graphical icon, a graphical mark, or the like, or any combination thereof. In some embodiments, the calculation package may include one or more algorithms, methods, processes, formulas, rules, or the like, or any combination thereof.

In some embodiment, processor 202 may utilize one or more of the imaging parameters, the display annotation, and/or the calculation package for further use for optimizing image segmentation or enhancing the image segmentation. For example, the imaging parameters, the display annotation, and/or the calculation package may be updated to storage 203 for further use.

Referring back to 1004, if the feature set is determined to have changed, processor 202 at 1009 may compare the extracted feature set with a feature set template. The feature set template may be structured in any configuration that may be accessed by processor 202 for image segmentation. Merely by way of example, the feature set template may include a table (e.g., a look-up table) of feature set, an algorithm representing a group of feature sets, a formula representing a group of feature sets, a rule representing a group of feature sets, or the like, or any combination thereof. The feature set template may be described elsewhere in the present disclosure.

At 1010, processor 202 may determine whether a new feature set has been identified. Merely by way of example, the new feature set may include a brightness, a size value, a shape of a segment, or the like, or any combination thereof.

If processor 202 does not determine a new feature set, processor 202 at 1011 may modify the existing image segments. In some embodiments, processor 202 may modify the existing image segments as a function of time. For example, the segments may be slowly or rapidly modified depending on a rate of change of the segments. At 1012, processor 202 may identify the imaging parameter(s) based on the modified image segments.

At 1013, processor 202 may slowly modify the identified imaging parameters with time. In some embodiments, processor 202 may modify the imaging parameters as a function of time. For example, the imaging parameters may be slowly or rapidly modified depending on a rate of change of the imaging parameters. At 1014, processor 202 may retain the display annotations and calculation packages.

Referring back to 1010, if processor 202 identifies a new feature set, processor 202 at 1015 may determine one or more new segments and/or one or more feature sets. In some embodiments, the new segment(s) and/or feature set(s) determined may be used as prior feature set(s) in step 1003.

At 1016, processor 202 may rapidly modify the imaging parameters with time. In some embodiments, processor 202 may modify the imaging parameters as a function of time. For example, the imaging parameters may be slowly or rapidly modified depending on a rate of change of the imaging parameters. At 1017, processor 202 may modify the display annotations and calculation packages.

In some embodiments, processor 202 may utilize one or more of the imaging parameter, the display annotation, and/or the calculation package for further use to optimize image segmentation or enhance the image segmentation. For example, the imaging parameters, the display annotation, and/or the calculation package may be updated to storage 203 for further use.

TABLE 1, TABLE 2, and TABLE 3 depict example logic tables for the method of FIG. 10 according to some embodiments. The logic table may include a feature set template, and a corresponding imaging parameter adjustment for each feature set. Merely by way of example, the feature set templates depicted in TABLE 1, TABLE 2, and TABLE 3 may be structured as look-up tables (LUT). TABLE 1 and TABLE 2 depict example feature set templates for the tissue version, and TABLE 3 depicts an example feature set template for the flow version.

TABLE 1 represents an LUT for identification and optimization for two-dimensional image segment. As illustrated In TABLE 1, the features extracted may include local brightness and local orientation. In the rows beneath the "local brightness" and "local orientation" titles, the various configurations are shown (e.g., a low local brightness and a medium local orientation, a medium local brightness, and a high local orientation, etc.). The demarcations for what constitutes "low," "medium," or "high" value may be based on a relative scale. Numerical representations (or other determining feature) of the features (e.g., low brightness may refer to brightness with a values less than or equal to a certain value) may vary based on the specific application. It should be understood that the relative scale depicted herein in regard to TABLE 1, TABLE 2, and TABLE 3 is meant to show an exemplary configuration. Other configurations with varying values or scales may also be contemplated.

TABLE 1

| Determined imaging feature | | | Imaging parameter to change | |
|---|---|---|---|---|
| Local brightness | Local orientation | Dynamic range | Persistence | Spatial Filter |
| Low | Low | Low | High | High |
| Low | Medium | Low | Medium | Directional filter |
| Low | High | Low | Low | Directional filter |
| Medium | Low | High | Medium | Medium |
| Medium | Medium | Medium | Medium | Medium |
| Medium | High | Low | Low | Directional filter |
| High | Low | Medium | Medium | Directional filter |
| High | Medium | Low | Medium | Directional filter |
| High | High | Low | Low | Directional filter |

As shown in TABLE 1, the imaging parameters may be adjusted based on the extracted local brightness and local orientation features. The imaging parameters maybe adjustable parameters/variables/coefficients used to decrease the noise in the image. Application of these parameters may lead to an enhancement of each image segment corresponding to each particular feature set. The exemplary imaging parameters in TABLE 1 may also include dynamic range, persistence, spatial filter, etc. An exemplary process for modifying the imaging parameters (e.g., processes 1006 and 1012 of FIG. 10) is described as follows: for a determined imaging feature set including low local brightness and low local orientation, the dynamic range, persistence, and spatial filter may be modified to "low," "high," and "high," respectively. In some embodiments, the LUT may include more, less, or different imaging parameters than those included in TABLE 1. In some embodiments, for each combination of the two-dimensional image features, processor 202 may modify one or more imaging parameters in accordance with the determined two-dimensional image features.

TABLE 2 illustrates an exemplary LUT for a four-dimensional image feature optimization. As illustrated in TABLE 2, the imaging features may include regional area, regional shape, structure brightness, and structure speckle content. The tissue type may be identified and the imaging parameter to be modified may be identified (e.g., processes 1012 and 1013 in FIG. 10) in accordance with the determined values for each imaging feature. In operation, TABLE 2 may include a series of rows with each combination of regional area, regional shape, structure brightness, and structure speckle content.

TABLE 2

| Segmented imaging feature | | | | | | Imaging parameter to change | | |
|---|---|---|---|---|---|---|---|---|
| Regional area | Regional Shape | Structure brightness | Structure speckle content | Tissue type identified | Imaging view identified | Dynamic range | Persistence | Spatial filter |
| Small/ Medium | Elongated/ Circular/ Tubular/ Elliptical/ Irregular | Low/ Medium/ High | Low/ Medium/ High | Carotid/ Thyroid/ Liver/ Kidney/ Heart/ Thigh/ Calf/etc. | LongAxis/ ShortAxis/ 4-chamber/ Etc. | Low/ Medium/ High | Low/ Medium/ High | Low/ Medium/ High |

In some embodiments, TABLE 1 and TABLE 2 may be used together for the identification and enhancement of image segment(s) (via TABLE 1) and the identification of tissue type(s) (via TABLE 2). Segmenting the image into tissue types may help in tissue adaptive processing. For example, the imaging parameters may be modified according to the segmented tissues. As still another example, the presets of imaging parameters may be determined and/or modified according to one segmented tissue among several segmented tissues.

Figure 11:
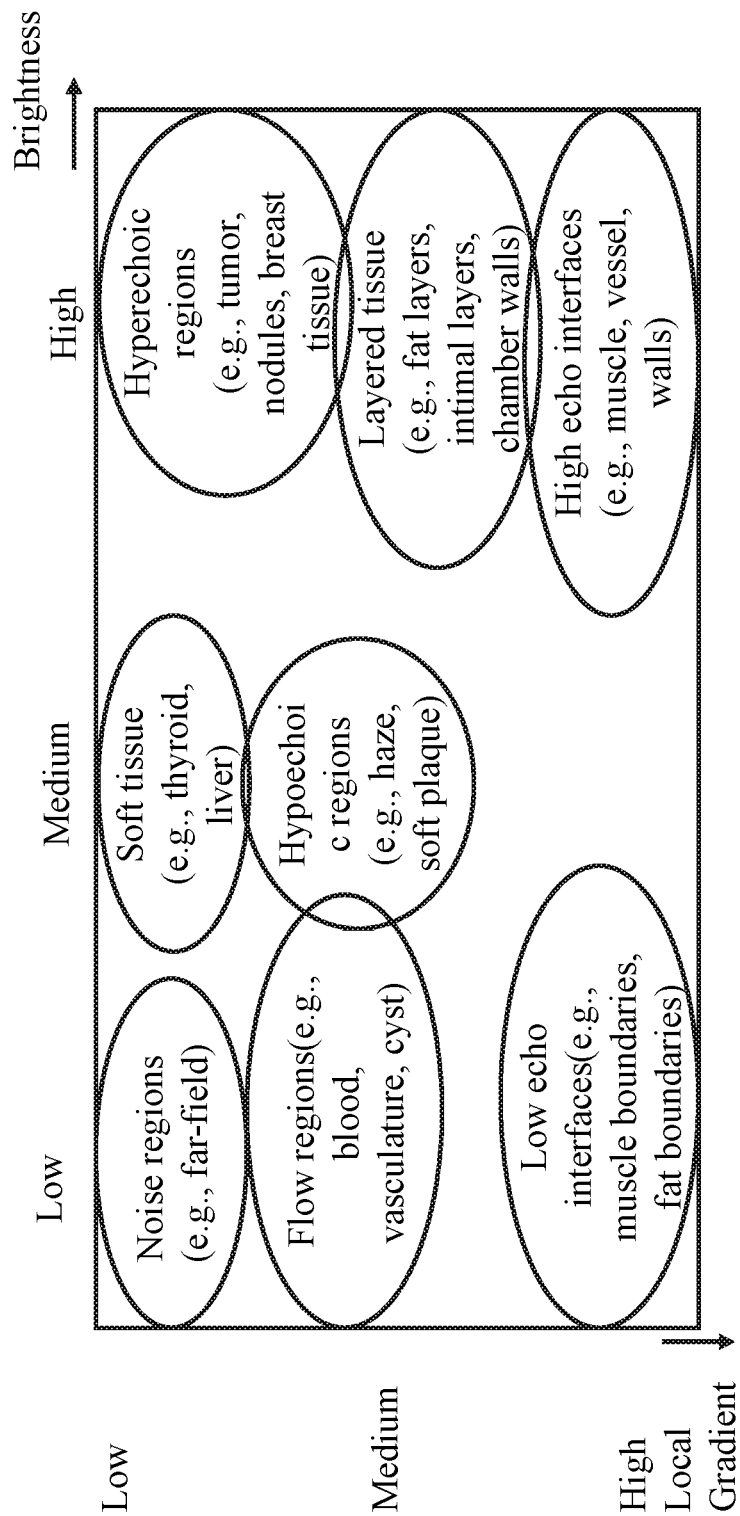
FIG. 11 is an exemplary image segmentation according to some embodiments.

FIG. 11 illustrates an example of an image segmentation according to some embodiments. As shown in FIG. 11, various segments of an image (e.g., soft tissue, layered tissue, etc.) may be identified wherein imaging parameters for each segment may be optimized appropriately via TABLE 1 and TABLE 2. The image segmentations may be determined based on brightness versus local gradient. For example, if an imaging object has high brightness, but low local gradient, the imaging object may be identified as a hyperechoic region for segmentation.

TABLE 3 depicts an exemplary feature set template for the flow version of an image. In some embodiment, TABLE 3 may be utilized with a Color Doppler and a PW Doppler imaging. The application of the table may be similar to that of TABLE 1 and TABLE 2. In some embodiments, TABLE 3 may include a six-dimensional image feature set including, for example, flow size, flow orientation (e.g., flow direction), flow gradient, flow time pattern, flow velocity, and flow power. Imaging parameters may be adjusted (e.g. dynamic range, persistence, spatial filter, etc.) in accordance with the determined combination of these features. For example, the dynamic range may be adjusted to "low," the persistence may be adjusted to "medium", and the spatial filter may be adjusted to "high," in accordance with the determined combination of features (e.g., a "low" flow size, a "medium" orientation, a "low" flow gradient, a "medium" flow time pattern, a "high" flow velocity, and a "medium" flow strength).

Figure 12:
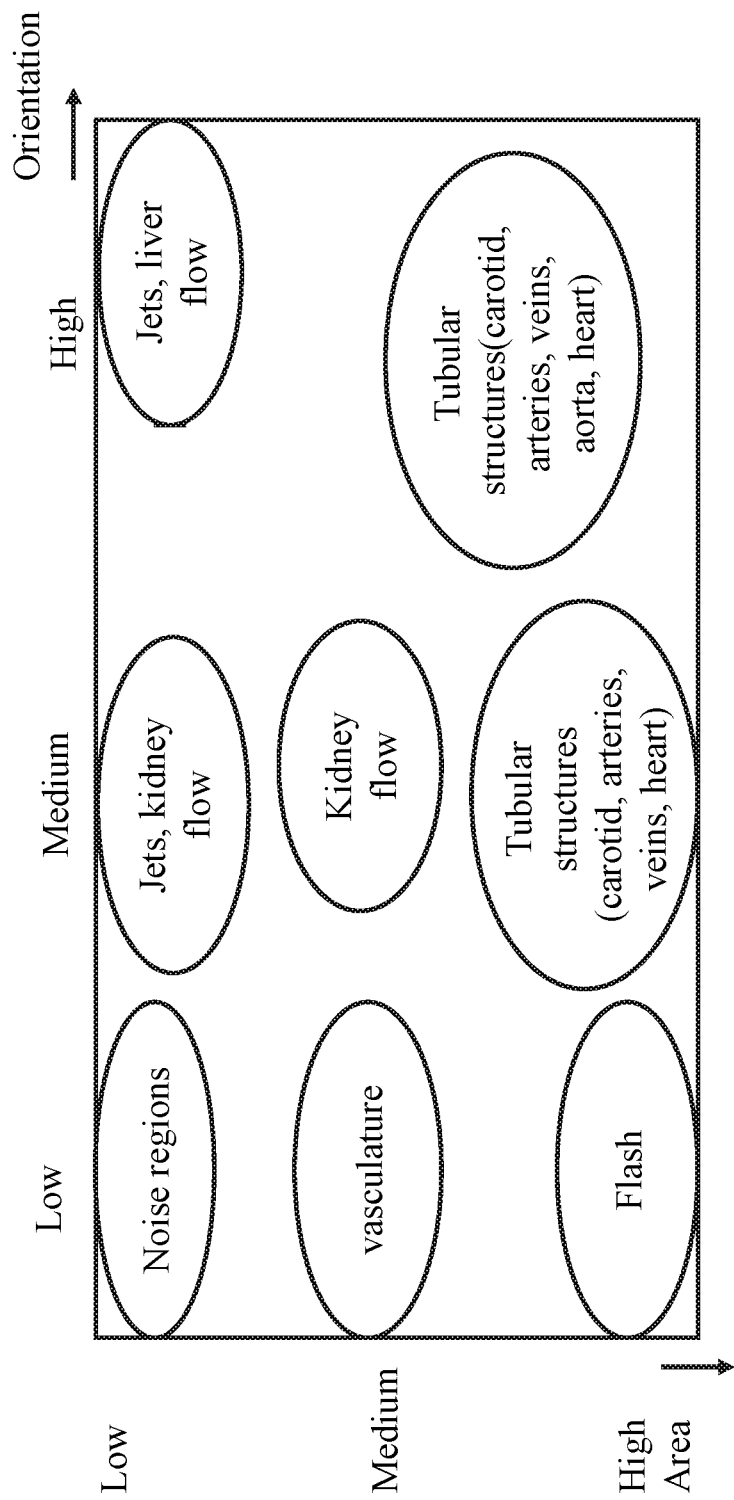
FIG. 12 is an exemplary image segmentation according to some embodiments.
Figure 13:
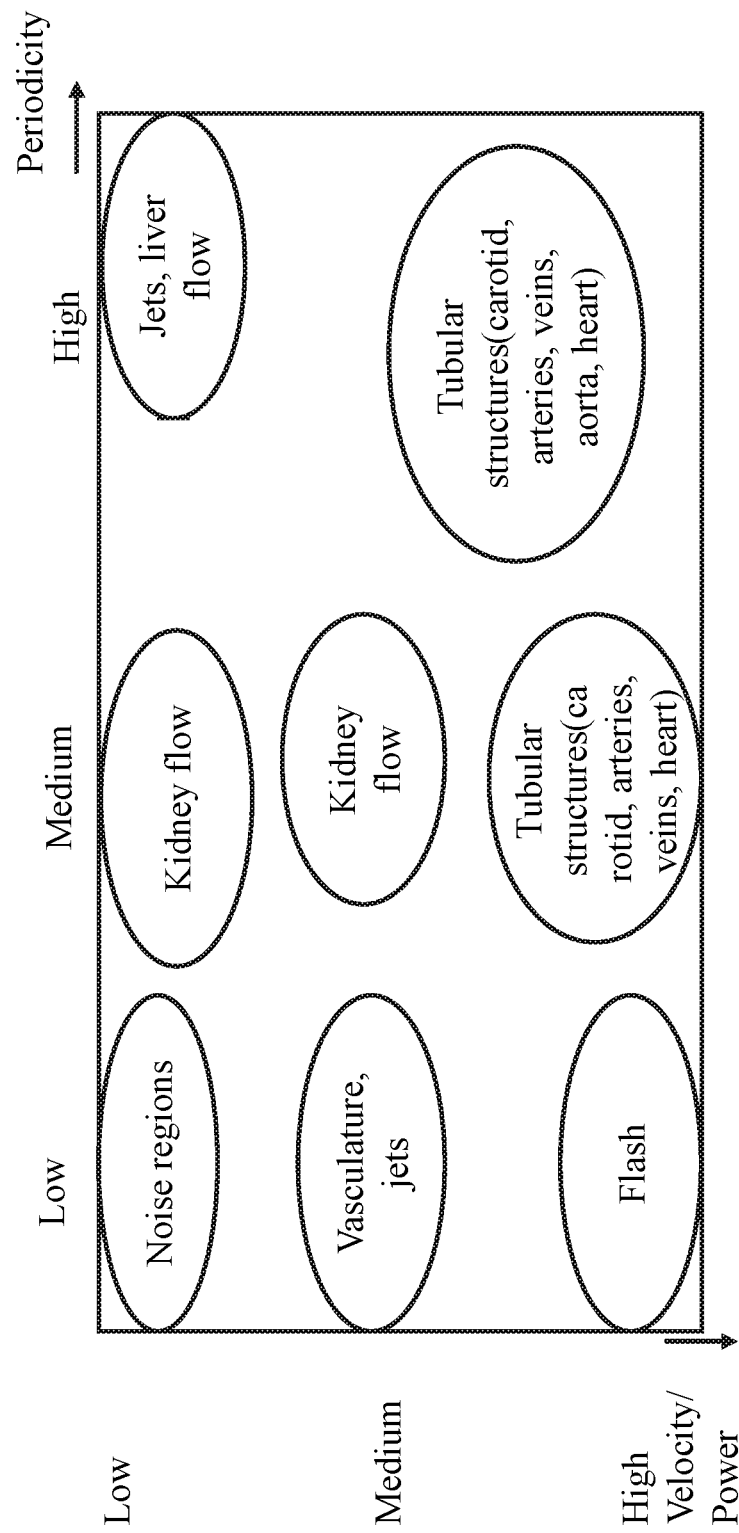
FIG. 13 is an exemplary image segmentation according to some embodiments.

FIG. 12 and FIG. 13 depict exemplary flow image segmentations according to some embodiments. Based on the flow segmentation, as mentioned above, the imaging parameters may be selected and applied appropriately. Similar to FIG. 11, FIG. 12 and FIG. 13 depict two dimensions of parameters. However, it should be understood that all six dimensions of image features may be utilized for segmenting and modifying the imaging parameters.

process for feature set extraction in a B-mode ultrasound. At 1401, processor 202 may determine one or more images. In some embodiments, the image(s) may be acquired from scanner 101, computing device 102 and/or server 104. For example, I/O 204 may receive the image(s) from scanner 101 and transmit the image(s) to processor 202 for image processing. In some embodiments, the image(s) may be stored in storage 203. For example, the image(s) may be pre-processed by processor 202 and stored in storage 203 for segmentation.

At 1402, processor 202 may determine one or more local parameters. In some embodiments, the local parameter(s) may include a local brightness and/or a local orientation. At 1403, processor 202 may segment the image based on the determined local parameters (e.g., local brightness and/or local orientation, etc.) into at least one region of the image. In some embodiments, processor 202 may segment the image based on local brightness and local orientation consecutively, or in parallel, or in any other orders. In some embodiments, image segmentation methods may include a wavelet transformation, a Gabor transform, a morphological image processing method, an image frequency domain processing method, a histogram-based method (e.g., color histogram-based method, intensity histogram-based method, edge histogram-based method, etc.), a compression-based method, a region-growing method, a partial differential equation-based method, a variational method, a graph partitioning method, a watershed transformation, a model-based segmentation method, a multi-scale segmentation, a triangulation method, a co-occurrence matrix method, an edge detection method, a threshold method, or the like, or any combination thereof.

At 1404, processor 202 may identify imaging regions from the segments. For example, processor 202 may identify the regions based on the brightness and orientation of the segments obtained at 1403. At 1405, processor 202 may compare the imaging regions identified at 1404 with region templates. In some embodiments, the region templates may be generated from prior imaging sets, user-defined templates, or other region templates. In some embodiments, processor 202 may use one or more algorithms, processes, formulas, rules, or the like to determine a degree of similarity between the identified imaging regions and existing imaging regions in the region templates.

At 1406, processor 202 may determine whether an identified imaging region matches with an imaging region in a

TABLE 3

| Determined imaging feature | | | | | | Imaging parameter to change | | |
|---|---|---|---|---|---|---|---|---|
| Flow size | Flow orientation | Flow gradient | Flow time pattern | Flow velocity | Flow strength | Dynamic range | Persistence | Spatial filter |
| Low/ Medium/ High | Low/ Medium/ High | Low/ Medium/ High | Low/ Medium/ High | Low/ Medium/ High | Low/ Medium/ High | Low/ Medium/ High | Low/ Medium/ High | Low/ Medium/ High |

It should be understood that FIG. 11, FIG. 12 and FIG. 13 provide only a few examples of the features. The feature set may include additional feature(s) such as the relative location of the features within the image, as well as the arrangement of the features to provide a topography or view of the imaged region to characterize certain region of interest.

Figure 14:
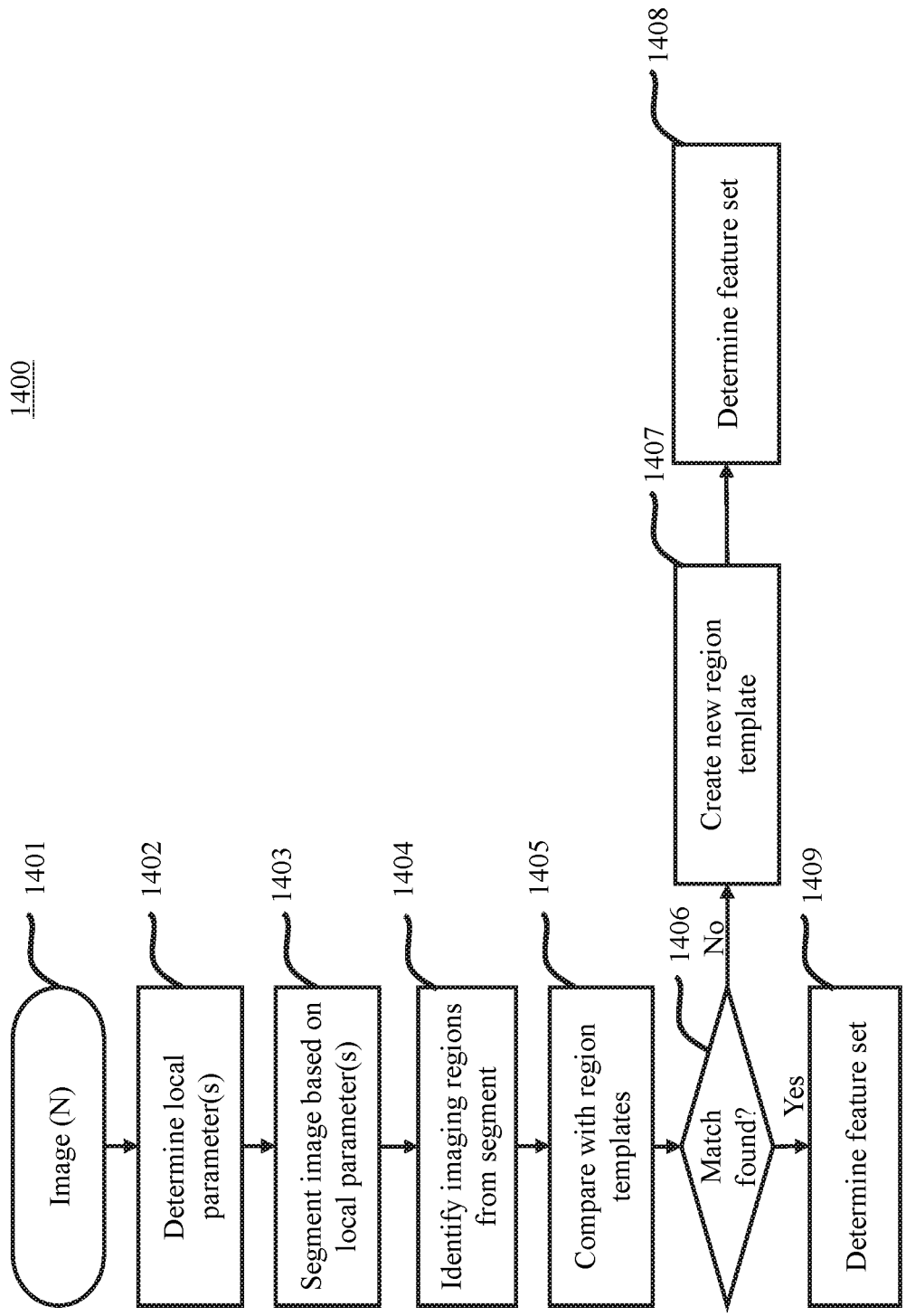
FIG. 14 is a flowchart of an exemplary process of feature set extraction according to some embodiments.

FIG. 14 is a flowchart of an exemplary process 1400 for extracting feature set, which may be used in step 1002 of process 1000 illustrated in FIG. 10, according to some embodiments. Specifically, FIG. 14 illustrates an exemplary region template. In some embodiments, processor 202 may determine whether the identified imaging region matches with the imaging region in the region template based on a degree of similarity between the region and the template. For example, if the difference between local brightness values in the identified imaging region and an imaging region in the region template are within five percent of each other, processor 202 may determine that the region matches with the region template. As another example, if the local gradients of the identified imaging region and an imaging region in the region template differ by more than ten percent at particular locations, processor 202 may determine that the region does not match with the region template. The criteria for determining whether there is a match for the region may be configurable. In some embodiments, the determination may be based on the difference of one image feature (e.g. brightness, contrast, or orientation) between the region identified and the region template. In some embodiments, the determination may be based on a plurality of image features (e.g. brightness, contrast, and orientation). The process for determining whether the identified imaging region matches with the region template may differ for different applications or scenarios (e.g. different locations on the body, different RF data, different purpose, different types of subjects, etc.). All such variations or modifications are intended to fall within the spirit and scope of the present disclosure.

If the identified imaging region does not match with the region template, at 1407, processor 202 may create a new region template. At 1408, processor 202 may determine the feature sets used at step 1003 of process 1000 illustrated in FIG. 10. In some embodiments, processor 202 may determine new feature sets based on the created new region template. Merely by way of example, the new feature sets determined may include an area, an orientation, a brightness, a speckle content, or the like, or any combination thereof. If the identified imaging region matches with the region template, at 1409, processor 202 may determine feature sets used at step 1003 of process 1000 illustrated in FIG. 10. Additionally or alternatively, processor 202 may determine feature sets based on the prior region template. Merely by way of example, the feature sets determined may include an area of an object, an orientation of an object, a local or overall brightness, a speckle content, or the like, or any combination thereof.

Figure 15:
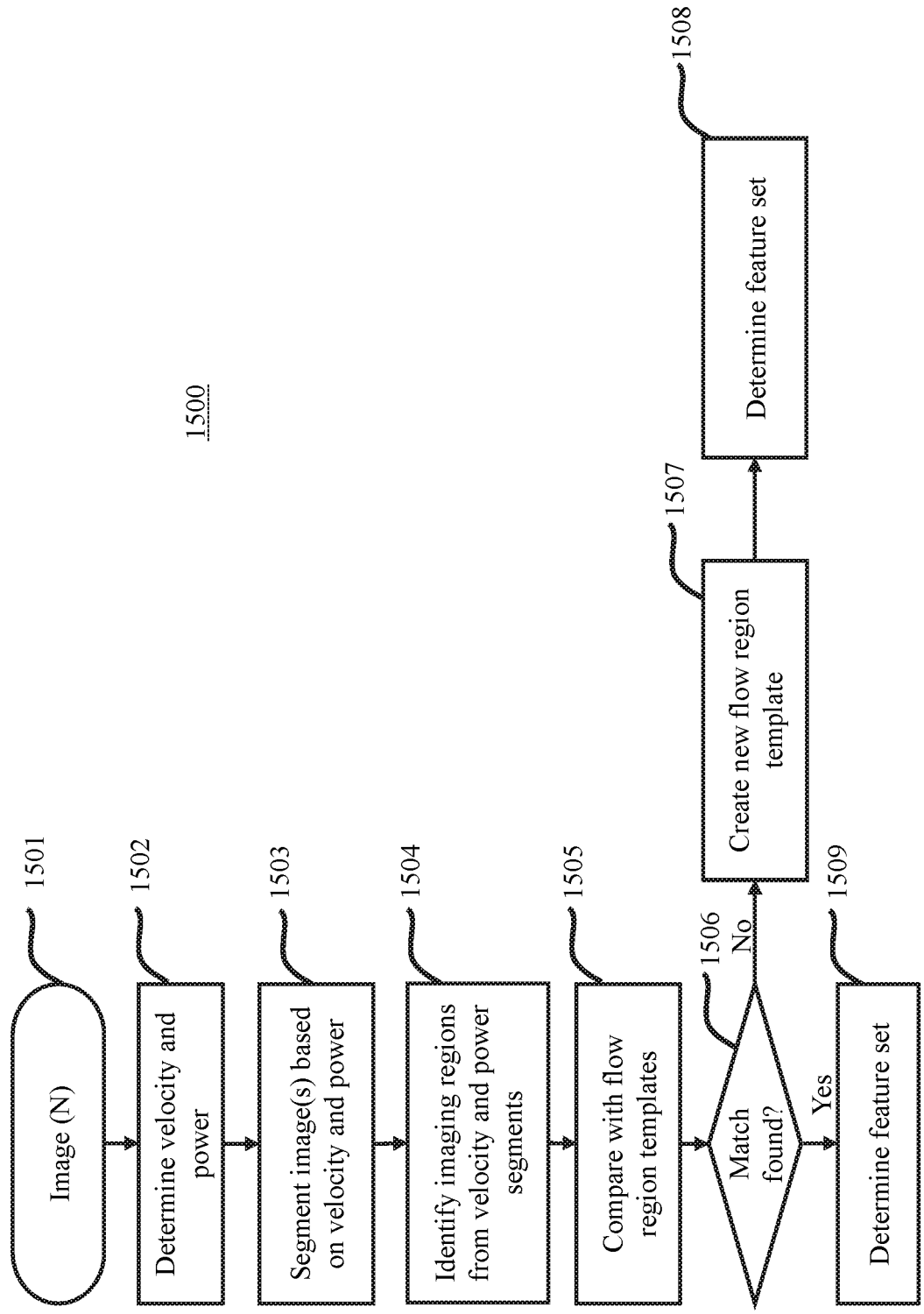
FIG. 15 is a flowchart of an exemplary process of feature set extraction according to some embodiments.

FIG. 15 is a flowchart of an exemplary process 1500 for feature set extraction, which may be used in step 1002 of process 1000 illustrated in FIG. 10, according to some embodiments. More specifically, FIG. 15 illustrates an exemplary process for feature set extraction in a C-mode ultrasound.

At 1501, processor 202 may identify one or more images. In some embodiments, the image(s) may be acquired from scanner 101, computing device 102 and/or server 104. For example, I/O 204 may receive the image(s) from scanner 101, and transmit the image(s) to processor 202 for image processing. In some embodiments, the image(s) may be stored in storage 203. For example, the image(s) may be pre-processed by processor 202 and stored in storage 203 for future segmentation.

At 1502, processor 202 may determine flow velocity and/or flow power in the image(s). At 1503, processor 202 may segment one or more images based on the determined flow velocity and/or flow power into at least one region of the image. In some embodiments, processor 202 may segment an image based on flow velocity and flow power consecutively. In some embodiments, processor may segment the image based on flow velocity and flow power simultaneously. In some embodiments, processor 202 may segment a multitude of images based on flow velocity and/or flow power. In some embodiments, image segmentation methods may include a wavelet transformation, a Gabor transform, a morphological image processing method, an image frequency domain processing method, a histogram-based method (e.g., color histogram-based method, intensity histogram-based method, edge histogram-based method, etc.), a compression-based method, a region-growing method, a partial differential equation-based method, a variational method, a graph partitioning method, a watershed transformation, a model-based segmentation method, a multi-scale segmentation, a triangulation method, a co-occurrence matrix method, an edge detection method, a threshold method, or the like, or any combination thereof.

At 1504, processor 202 may identify imaging regions from the velocity segments and power segments. At 1505, processor 202 may compare the identified imaging region with region templates. The region templates may be saved in a region database or storage 203 located in computing device 102 or server 104. In some embodiments, the region templates may be generated from prior imaging sets, user defined templates, or other sources. In some embodiments, processor 202 may use one or more algorithms, processes, rules, formulas, or the like to determine a degree of similarity between the identified imaging regions and the region templates.

At 1506, processor 202 may determine whether an identified imaging region matches with a certain region in a region template. In some embodiments, processor 202 may determine whether the identified imaging region matches with the region template based on a degree of similarity between the identified imaging region and the region template. For example, if the differences between any two among multiple flow velocities at particular locations are within five percent of each other, the processor 202 may determine that the region matches with the region template. As another example, if the flow powers of the identified imaging region and the region template differ by more than ten percent at particular locations, processor 202 may determine that the region does not match with the region template. The criteria for determining whether there is a match for the region may be configurable. In some embodiments, the determination may be based on the difference of one image feature (e.g. flow velocity or flow power) between the imaging region identified and the region template. In other embodiments, the determination may be based on a plurality of image features (e.g. flow velocity and flow power). The process for determining whether the identified imaging region matches with the region template may differ for different applications or scenarios (e.g. different locations on the body, different RF data, different purpose, different types of subjects, etc.). All such variations or modifications are intended to fall within the spirit and scope of the present disclosure.

If the identified imaging region does not match with the region template, at 1507, processor 202 may create a new region template. At 1508, processor 202 may determine the feature sets used at step 1003 of process 1000 illustrated in FIG. 10. In some embodiments, processor 202 may determine new feature sets based on the created new region template. Merely by way of example, the new feature sets determined may include a size of an object, a contour of an object, an orientation of an object, a local or overall gradient, a time pattern, a flow velocity, a flow power, or the like, or any combination thereof. If the identified imaging region matches with one region in the region template, at 1509, processor 202 may determine feature sets used at step 1003 of process 1000 illustrated in FIG. 10. Additionally or alternatively, processor 202 may determine feature sets based on the prior region template. Merely by way of example, the feature sets determined may include a size of an object, a contour of an object, or an orientation of an object, a local or overall gradient, a time pattern, a flow velocity, a flow power, or the like, or any combination thereof.

Figure 16:
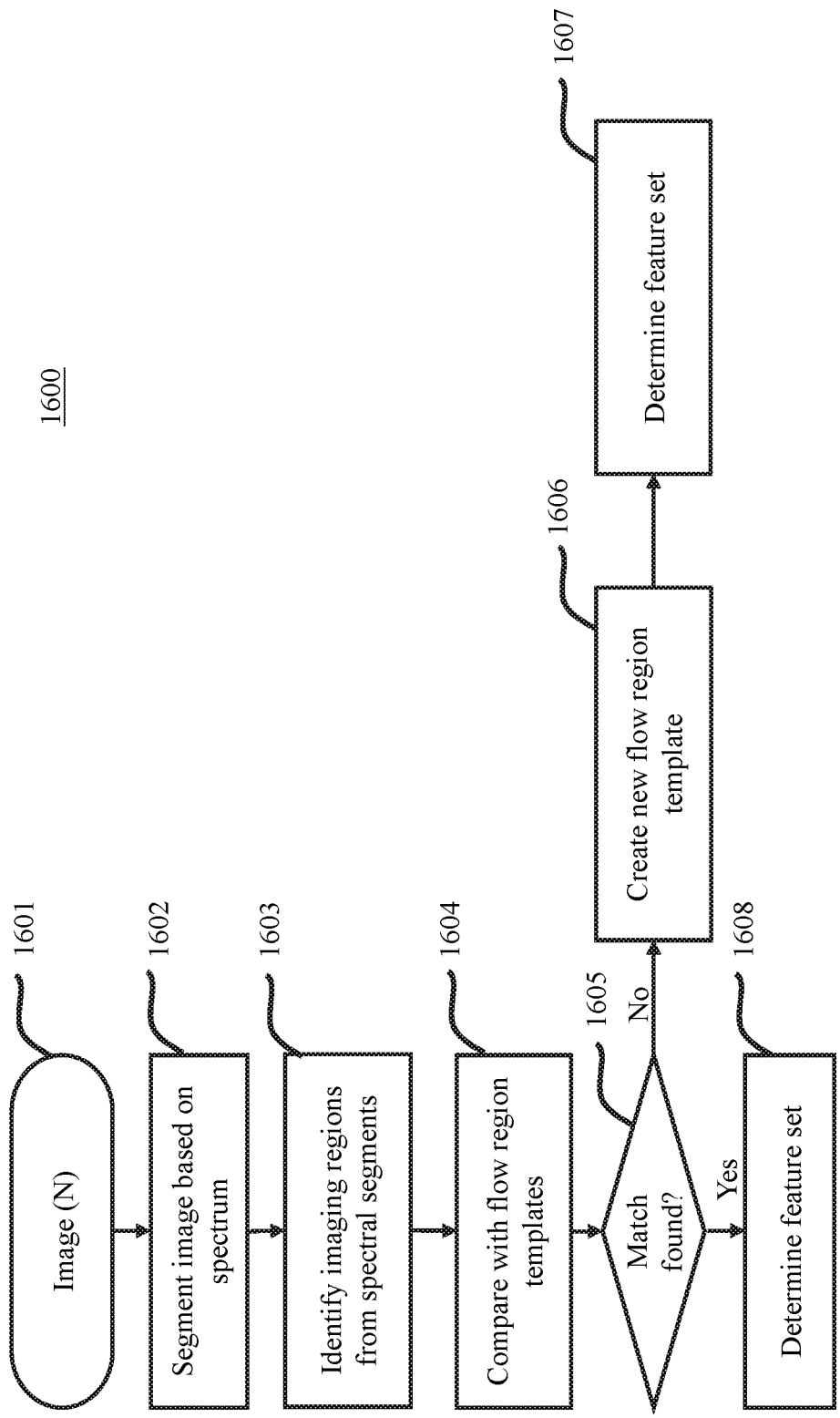
FIG. 16 is a flowchart of an exemplary process of feature set extraction according to some embodiments.

FIG. 16 is a flowchart of an exemplary process 1600 for feature set extraction, which may be used in step 1002 of process 1000 illustrated in FIG. 10, according to some embodiments. More specifically, FIG. 16 illustrates an exemplary process for feature set extraction in a PW-mode ultrasound.

At 1601, processor 202 may identify one or more images. In some embodiments, the image(s) may be acquired from scanner 101, computing device 102 and/or server 104. For example, I/O 204 may receive the image(s) from scanner 101, and transmit the image(s) to processor 202 for image processing. In some embodiments, the image(s) may be stored in storage 203. For example, the image(s) may be pre-processed by processor 202 and stored in storage 203 for segmentation.

At 1602, processor 202 may segment the image based on its spectrum into at least one region of the image. At 1603, processor 202 may identify imaging regions from the spectral segments segmented at step 1602. At 1604, processor 202 may compare the identified imaging regions with flow region templates. In some embodiments, the flow region templates may be generated from prior imaging sets, user defined templates, or other sources. In some embodiments, processor 202 may use one or more algorithms, processes, formulas, rules, or the like to determine a degree of similarity between the identified imaging regions and the region templates.

At 1605, processor 202 may determine whether an identified imaging region matches with a region template. In some embodiments, processor 202 may determine whether the identified imaging region matches with the region template based on a degree of similarity between them. For example, if the differences between any two among multiple spectrums at particular locations of the identified imaging region and the region template are within five percent of each other, processor 202 may determine that the region matches with the region template. As another example, if the spectrums of the identified imaging region and the region template differ by more than ten percent at particular locations, processor 202 may determine that the region does not match with the region template. The criteria for determining of whether there is a match for the region may be configurable. The process for determining whether the identified imaging region matches with the region template may differ for different applications or scenarios (e.g. different locations on the body, different RF data, different purpose, different types of subjects, etc.). All such variations or modifications are intended to fall within the spirit and scope of the present disclosure.

If the identified imaging region does not match with the region template, at 1606, processor 202 may create a new region template. At 1607, processor 202 may determine the feature sets used at step 1003 of process 1000 illustrated in FIG. 10. In some embodiments, processor 202 may determine new feature sets based on the created new region template. Merely by way of example, the new feature sets determined may include a local or overall gradient, a time pattern, a flow velocity, a flow power, or the like, or any combination thereof. If the identified imaging region matches the region template, at 1608, processor 202 may determine feature sets used at step 1003 of process 1000 illustrated in FIG. 10. Additionally or alternatively, processor 202 may determine feature sets based on the prior region template. Merely by way of example, the feature sets determined may include a local or overall gradient, a time pattern, a flow velocity, a flow power, or the like, or any combination thereof. The newly created region template may be stored in computing device 102 and/or server 104.

Application of the User Interface Model

Figure 17:
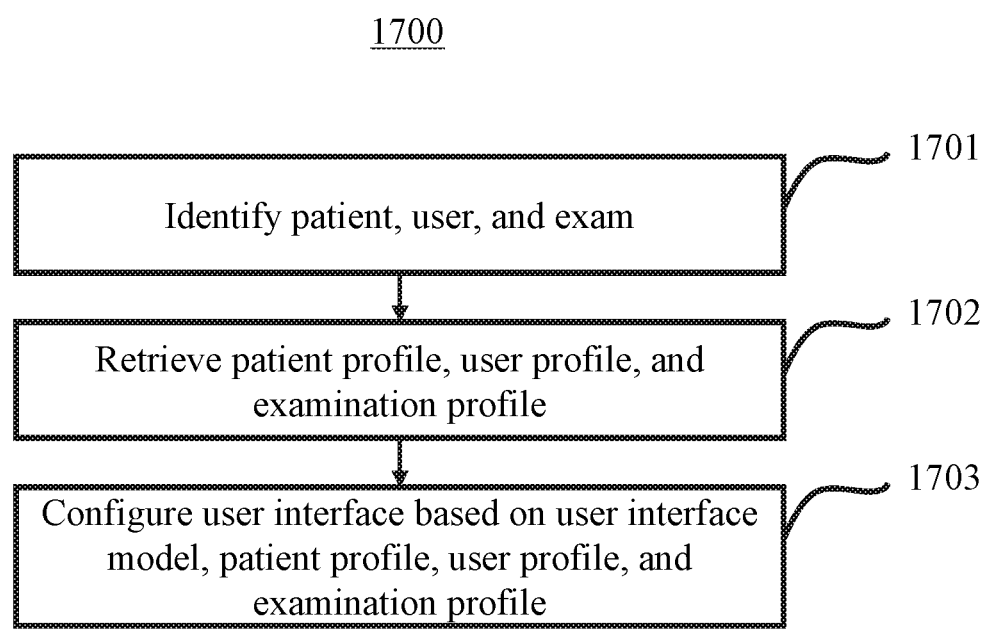
FIG. 17 is a flowchart of an exemplary process for applying the model of user interface according to some embodiments.

FIG. 17 is a flowchart of an exemplary process 1700 for applying the user interface model, which may be used in step 303 of process 300 illustrated in FIG. 3, according to some embodiments. At 1701, processor 202 may identify a user, a patient, and/or an examination. In some embodiments, processor 202 may identify the user, and/or the patient from a patient's demographic page. In some embodiments, processor 202 may identify the user, and/or the patient from a hospital network. For example, processor 202 may identify the user, and/or the patient from a schedule (e.g., a user schedule, a patient schedule, an examination schedule, etc.) in the hospital network.

At 1702, processor 202 may retrieve the user profile, the patient profile, and/or the examination profile. In some embodiments, the user profile, the patient profile, and/or the examination profile may include personal data associated with user, a patient, and/or an examination. Merely by way of example, the user profile may include a user's identity, and/or a user's preferences. The patient profile may include a patient's identity, and/or a patient's preferences. The examination profile may include an examination type, and/or or an examination preferences, etc.

At 1703, processor 202 may configure the user interface based on the user interface model, and/or the user profile, and/or the patient profile, and/or the examination profile. For example, the location of certain functions on a touch screen interface may be configured according to the user interface model, the user, the patient, and/or the examination. In some embodiments, one or more functions may be initiated by the user instruction (e.g., pressing short-keys, etc.). For example, the user may manually configure the instructions to perform the functions.

In some embodiments, storage 203 may store the preset configurations and/or data of user interface saved by the user. In some embodiments, processor 202 may present the previously saved user interface configuration and data to the user. In some embodiments, processor 202 may present a recommendation of a most common user interface preset to the user. The most common user interface preset may be chosen based on the usage frequency or probability for the user or similar users. Alternatively or additionally, the most common user interface preset may be chosen based on the usage frequency or probability for the patient or similar patients. Alternatively or additionally, the most common user interface preset may be chosen based on the usage frequency or probability of the examination or similar examinations. In some embodiments, processor 202 may allow the user to configure his/her user interface manually by providing a configuration interface on the screen. The manually configured user interface may be saved in the storage 203 or the server 104. The saved user interface may be used as presets. In some embodiments, processor 202 may update the user interface model according to the saved user interface.

In some embodiments, processor 202 may loop one or more steps in process 1700 to obtain a model. In some embodiments, processor 202 may implement one or more steps in process 1700 consecutively, or in parallel, or in any other orders.

Figure 18:
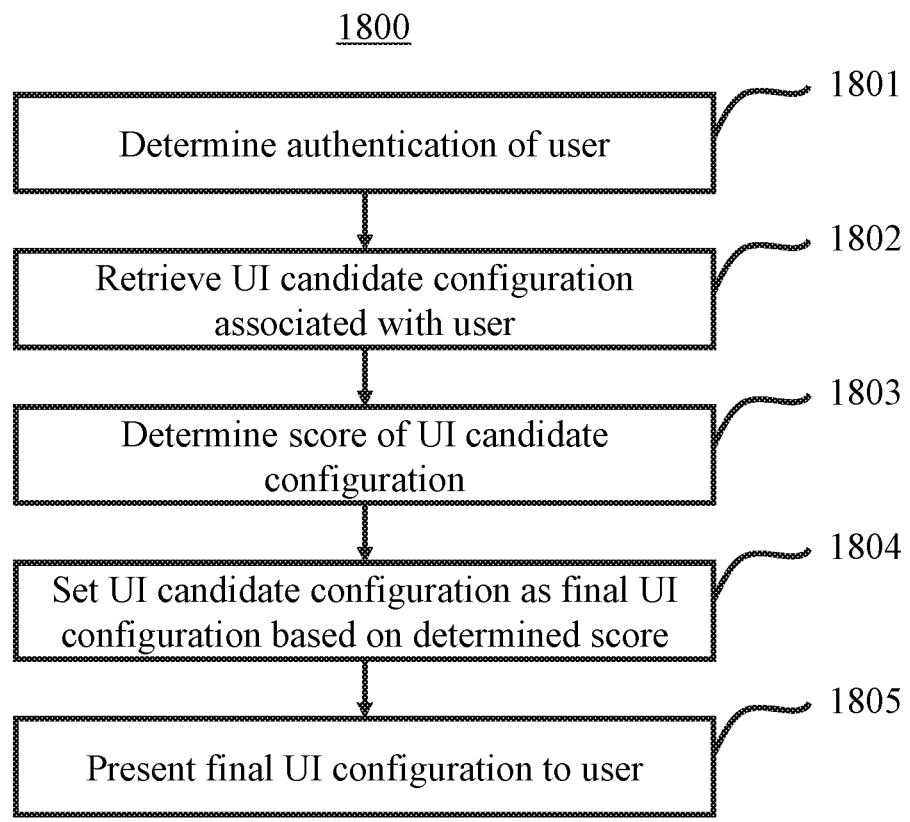
FIG. 18 is a flowchart of an exemplary process of user interface customization according to some embodiments.

In some embodiments, process 1700 may be performed according to an exemplary process for customizing the user interface illustrated in FIG. 18. FIG. 18 is a flowchart of an exemplary process 1800 for customizing the user interface according to some embodiments. At 1801, processor 202 may determine an authentication of a user. In some embodiments, the authentication process may be based on a login. For example, processor 202 may receive a user name and password via a keyboard, a touch screen, etc. As another example, processor 202 may authenticate a user through a biometric identification device, such as, a voice recognition device, a face recognition device, a finger print recognition device, an iris recognition device, etc. As still another example, processor 202 may identify a user through a barcode or quick response (QR) code scanner.

At 1802, processor 202 may retrieve (or generate ad-hoc) user interface candidate configuration associated with the user. In some embodiments, the user interface candidate configuration may be retrieved among one or more user interface configurations associated with the user. In some embodiments, the user may include an individual and/or a group of users.

At 1803, processor 202 may determine score of the UI candidate configuration. In some embodiments, the score of the UI candidate configuration may be represented as a ranking, a frequency of usage, or a probability of usage for user interface configuration candidate, etc. The score may be a combination of the ranking, frequency of usage or probability of usage for user interface candidate configuration. Merely by way of example, different locations of a button on the screen may indicate different frequency of usage or probabilities for different users. For example, to a user, and/or a large population of users, the frequency of usage for a power-on button placed on the lower, left portion of the screen may be 56%; the frequency of usage for the power-on button placed on the upper, left portion of the screen may be 24%; the frequency of usage for the power-on button placed on the middle portion of the screen may be 9%.

At 1804, processor 202 may set the user interface candidate configuration as a final UI configuration based on the determined score of the UI candidate configuration. In some embodiments, processor 202 may set the user interface candidate configuration having a certain score (e.g., a highest frequency of usage, a lowest frequency of usage, a middle frequency of usage, a top ranking, a middle ranking, a low ranking, etc.) as the final UI configuration. In some embodiments, processor 202 may customize the user interface configuration with most often used features at most prominent locations. For example, processor 202 may set the power-on button on the lower left of the screen having the highest frequency of usage of 56% as the final user interface configuration. In some embodiments, processor 202 may set more than one final user interface configuration.

At 1805, processor 202 may present the one or more final user interface configurations to the user. In some embodiments, processor 202 may present the final user interface configuration(s) with the certain score(s) (e.g., certain frequency of usage, certain probability, certain ranking, etc.). For example, processor 202 may present the power-on button placed on the lower, left portion of the screen, which has the highest probability on the screen to the user. In some embodiments, processor 202 may present an option for the user to select a user interface configuration. For example, processor 202 may present a drop-down menu of the user interface configurations for the user to select one of the user interface configurations. In some embodiments, processor 202 may present an optional "most common practice" user interface configuration to the user based on the data collected from the user, and/or a group of similar users.

In some embodiments, processor 202 may determine the customized user interface to be presented to the user according to one or more rules or criteria. For example, the customized user interface may be the most commonly used user interface based on data from an individual user, the most commonly used user interface based on data from one or more users in the same class or a group of the individual users. In some embodiments, the customized user interface may be the most commonly used user interface by the individual user in the past, for example, the last two months, the last one year, etc. In some embodiments, the customized user interface may be the most recently used user interface by the individual user. In some embodiments, the customized user interface may be the most recently saved user interface by the individual user. In some embodiments, the customized user interface may be determined according to the frequency of soft keys being pressed by the individual user, the users in the same class, or a group of the individual users.

In some embodiments, processor 202 may loop one or more steps in process 1800 to obtain a model. In some embodiments, processor 202 may implement one or more steps in process 1800 consecutively, or in parallel, or in any other orders.

Figure 19:
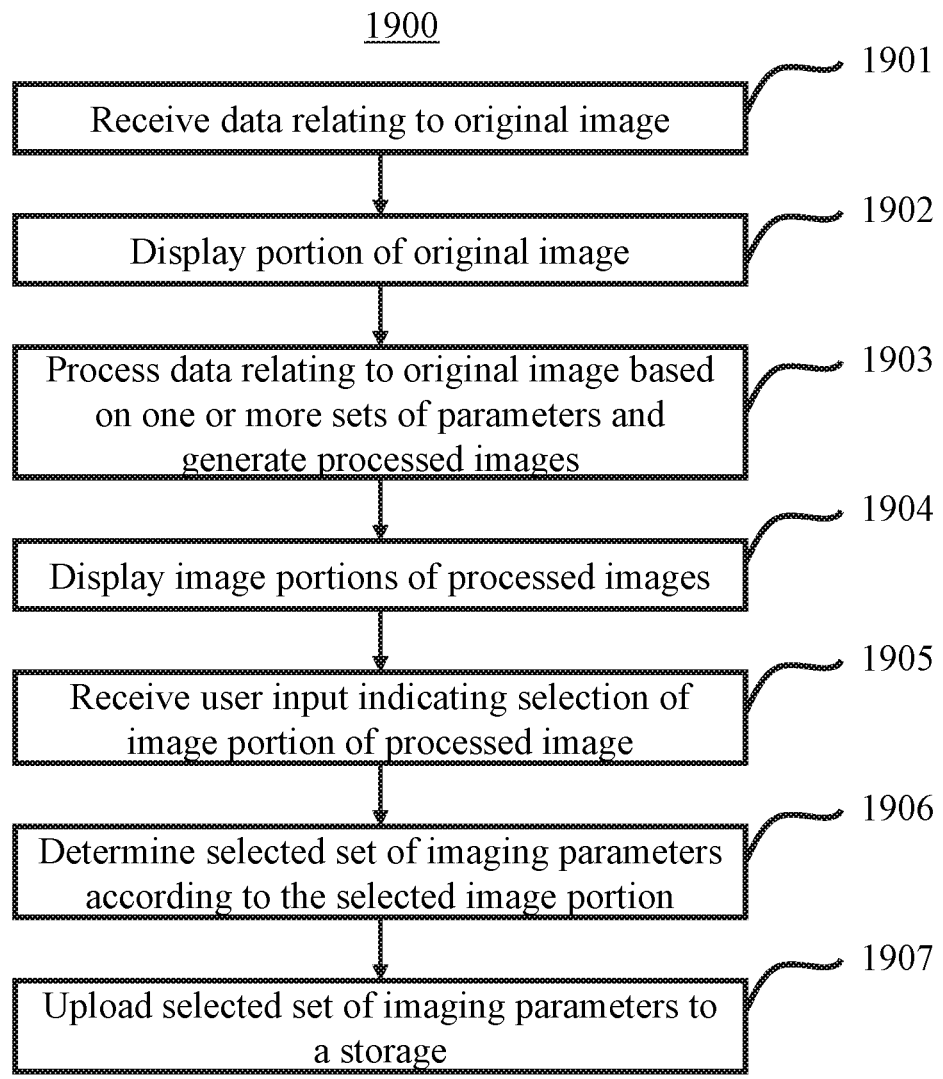
FIG. 19 is a flowchart of an exemplary process of image optimization according to some embodiments.

In some embodiments, the imaging parameters determined at step 904 of process 900 illustrated in FIG. 9 may be displayed on the user interface for image optimization according to an exemplary process illustrated in FIG. 19. FIG. 19 is a flowchart of an exemplary process 1900 for image optimization according to some embodiments. In some embodiments, image quality and imaging parameters may be determined by receiving feedback from the user. For example, the user may determine among a number of processed images (e.g., 5-12 processed images) to determine the imaging parameter(s) of the displayed image that provides the image preferred by the user. The processed images may be generated by applying different imaging parameters (e.g., spatial filter, dynamic range, persistence, etc.) on an original image of an object acquired from one or more components of computing system 100 (e.g., scanner 101, computing device 102, and/or server 104, etc.). In some embodiments, variations would be made in one or more imaging parameters that are not involved in the acquisition of ultrasound data. These imaging parameters (for example but not limited to boundary detection, spatial smoothing, white balance, dynamic range, persistence, gain, gray map, speckle reduction processing, edge enhancement processing and spatial filters) may be set to different sets of configurations to produce different images from the same ultrasound data. In some embodiments, the imaging parameters may also include different sets of configurations (e.g., an IIR filter may be used instead of a FIR filter) to produce different images from the same ultrasound data. In some embodiments, the I/O 204 of computing system 100 may present one or more images to the user. The user may give feedback to one or more components of computing system 100 (e.g., scanner 101, computing device 102, and/or server 104) based on the present image(s). In some embodiments, the feedback may include any user behaviors (e.g., choosing an image, saving an image, deleting an image, rating an image, commenting on an image, reordering a number of images, clicking somewhere on the screen, pressing a button, adjusting a user control, etc.) or any adjustment by user relating to the examination or the image. For example, information relating to adjustment by user or another user (for example, a selected imaging preset, changing of depth, speckle reduction, change of focal depth, change of frame rate etc.) may be used to select appropriate sets of imaging parameters for the specific imaging situation and in subsequent situations where some of those controls have also been adjusted. Computing system 100 may receive the feedback. Computing system 100 may use the feedback to determine a preset of one or more components or configurations of computing system 100 (e.g., scanner 101, computing device 102, and/or server 104), an option displayed the next time when the user is asked to choose the preferred image. In some embodiments, processor 202 may identify the user's selection by detecting the user's response to the processed image (e.g., saving the image and/or saving a clip of the image sequence). In some embodiments, I/O 204 may include several displays to streamline the choice of saving the image and/or the clip. For illustration purpose only, a method of using two displays (e.g., a first screen and a second screen) for determining an image preferred by the user is described below.

Referring back to FIG. 19, at 1901, processor 202 may receive data relating to an original image. In some embodiments, the original image may include metadata. The metadata may include information relating to the scenario in which the original image is acquired (e.g. the date, the location, resolution of the original image, settings of the image acquisition device, etc.) The metadata may include information relating to the examination (e.g., a patient information, a user information, an examination type, etc.). In some embodiments, the user may configure computing system 100 before the examination. For example, the user may set computing system 100 in a condition (such as, activation of graphic processing unit) that is preferred by the user for conducting an examination. In some embodiments, the original image may be received from a single ultrasound imaging system, or multiple ultrasound imaging systems. In some embodiments, processor 202 may receive the original image during the down-time of scanner 101. Alternatively or additionally, processor 202 may perform one or more steps in process 300 during the work-time of scanner 101. For example, the original image may be a live image. The live image may be captured, represented, or processed concurrently with the imaging, for example, an ultrasound diagnosis.

In some embodiments, processor 202 may receive a user instruction to store the original image. In some embodiments, the user instruction may be provided by the user via I/O 204 (e.g., sliding a slider, pushing a bar, pressing a button or key, clicking or touching at a certain position on the display, or the like).

At 1902, I/O 204 may display a portion of the original image. In some embodiments, the original image may be displayed in a window on the display. Merely by way of example, the first screen may display the portion of the original image in a pan box. In some embodiments, the user may position the pan box over a tissue of interest displayed on the first screen using a track ball, a touch pad, a touch screen, a keyboard, or the like, or any combination thereof. In some embodiments, processor 202 may present an option to the user to resize the pan box. In some embodiments, the portion of the original image may be the entirety or a part of the original image. In some embodiments, I/O 204 may display the portion of the original image in a first scale. The first scale may be 1:1, 1:5, 1:10, or any other suitable scale. In some embodiments, the portion of the original image may be created by portion of the original image data. In some embodiments, the portion of the original image may be created by the whole data of the original image. The portion of the original image may have a first resolution.

At 1903, processor 202 may process the data relating to the original image based on one or more sets of imaging parameter(s) and generate one or more processed images. In some embodiments, the sets of imaging parameter(s) may be determined at step 904 of process 900 illustrated in FIG. 9. In some embodiments, the one or more sets of imaging parameters may include three or more sets of imaging parameters. In some embodiments, the one or more sets of imaging parameters may include a preset set of imaging parameters. In some embodiments, portions rather than the entirety of the original image may be processed. In some embodiments, one or more portions of the processed images may be displayed. In some embodiments, the one or more sets of imaging parameters may be determined based on demographic information associated with the patient and/or the original image. The patient may be the subject of the imaging. In some embodiments, the demographic information may include a gender, an age, a birthday, a height, a weight, a blood type, a gestational age, or the like. In some embodiments, processor 202 may determine the sets of imaging parameters based on user input from a single ultrasound imaging system. Alternatively, processor 202 may determine the sets of imaging parameters based on user input from multiple ultrasound imaging systems that communicate with a server or each other via the Internet to exchange information or data.

At 1904, I/O 204 may display image portions of the processed images to the user. In some embodiments, I/O 204 may also display the sets of imaging parameters to the user. In some embodiments, the second screen may display the image portions of the processed images side-by-side, for example, in an array, a line, or a column. For example, the second screen may display the image portions of the processed images side-by-side. In some embodiments, the second screen may display the image portions of the processed images with different sets of imaging parameters. In some embodiments, the image portion of the processed image may be assigned a reference number, a key or a button for identifying by the user. In some embodiments, the user may adjust the imaging parameters for adjusting the display of the image portions of the processed images. In some embodiments, the image portion of the processed image may be the entirety or a part of the processed image. In some embodiments, I/O 204 may display the image portion of the processed images in a second scale. In some embodiments, the second scale may be equal to the first scale. In some embodiments, the second scale may be larger or smaller than the first scale. The second scale may be 1:1, 1:5, 1:10, or any other suitable scale. The image portions presented side-by-side may have a second resolution. The second resolution may be smaller or larger than the first resolution. For example, the image portions may be displayed in a magnified or reduced resolution, compared to the original image. In some embodiments, the second resolution may be equal to the first resolution. For example, the image portions may be displayed in a full resolution, compared to the original image.

In some embodiments, the user may select and save an image portion of a processed image among a number of the image portions of processed images displayed on the second screen. In some embodiments, the selection may be made by the user via I/O 204 (by, for example, clicking or touching on the screen, typing a reference number of an image, pressing a key or button corresponding to an image, etc.). In some embodiments, the user may further make additional post-processing or adjustment to the processed image after selecting an image portion of a processed image. In some embodiments, the user's selection of processed image may be useful for processor 202 to determine predetermined sets of imaging parameters when processing images. The user's adjustment be useful for processor 202 to modify or make variations to the sets of parameters or processing methods.

At 1905, processor 202 may receive a user input indicating a selection of an image portion of a processed image. In some embodiments, the user input may be indicative of one or more following: modifying the selected image portion or the entire processed image, making adjustments to the selected image portion or the entire processed image, storing the image portion of the processed image or the entire processed image, printing the image portion of the processed image or the entire processed image, and including the image portion of the processed image or the entire processed image to a report, or the like, or any combination thereof.

At 1906, Processor 202 may determine a selected set of imaging parameters according to the selected image portion.

At 1907, processor 202 may upload the selected image portion and/or the selected set of imaging parameters to storage 203, and/or server 104. In some embodiments, processor 202 may upload the metadata of the processed image to storage 203. For example, processor 202 may upload the set of the imaging parameters along with the examination type, the patient's demographic information (e.g., gender, age, birthday, height, weight, blood type, gestational age, etc.), the adjusted parameters, or the like, or any combination thereof. In some embodiments, processor 202 may also upload the position and/or the size of the pan box to storage 203.

In some embodiments, the information uploaded to storage 203 may be used by processor 202 for determining user preference for image quality, image processing or image enhancement. In some embodiments, the information uploaded to storage 203 may be used for predicting the preset and/or the options displayed next time for the user to process or enhance images. In some embodiments, the image quality may be dependent on an image depth, an image gain, a depth gain compensation (DGC) setting, a position of the variation pan box, or the like, or any combination thereof.

In some embodiments, process 1900 may be used for generating training sets fed into the process for obtaining a model for image enhancement. In some embodiments, the original image, the one or more sets of imaging parameters, the processed images, the selected image portion, and/or the selected set of imaging parameters may be fed into processor 202 as training sets. In some embodiments, the original image may be treated as the input. In some embodiments, the one or more processed images may be treated as the actual output. In some embodiments, the selected image portion may be treated as the desired output.

In some embodiments, the original image may be a motion picture. An motion picture image may include multiple frames. In some embodiments, I/O 204 may display one or more image portions of multiple frames of the original image to the user continuously. The one or more image portions of frames may be displayed in a temporal order. In some embodiments, the user may stop the continuous display of the multiple frames of the original image by providing a first user input. For example, the user input may include a depression of a freeze button, a click in the graphical user interface on the screen, etc.

I/O 204 may receive the first user input to stop displaying the multiple frames of the original image and to display a frame of the multiple frames. In some embodiments, I/O 204 of the system may display the frame of multiple frames of the original image via a first screen. Processor 202 may process the frame and generate one or more processed frames based on the one or more sets of imaging parameters. After the one or more processed frames are generated, I/O 204 may display one or more image portions of the one or more processed frames to the user via the first screen or a second screen.

The I/O 204 may receive a second user input indicating a selection of an image portion of a processed frame from the displayed one or more image portions of the one or more processed frames. The user input may include a click or touch on the screen, typing a reference number of the processed frame, pressing a key or button corresponding to the processed frame, etc. Processor 202 may determine a selected set of imaging parameters according to the selected image portion of the processed frame. For example, the selected set of imaging parameters may include a selected brightness, contrast, image quality, etc. Processor 202 may upload the selected set of imaging parameters to a server for storage. The stored set of imaging parameters may be used to determine or update the user preference.

Application of the Workflow Model

Figure 20:
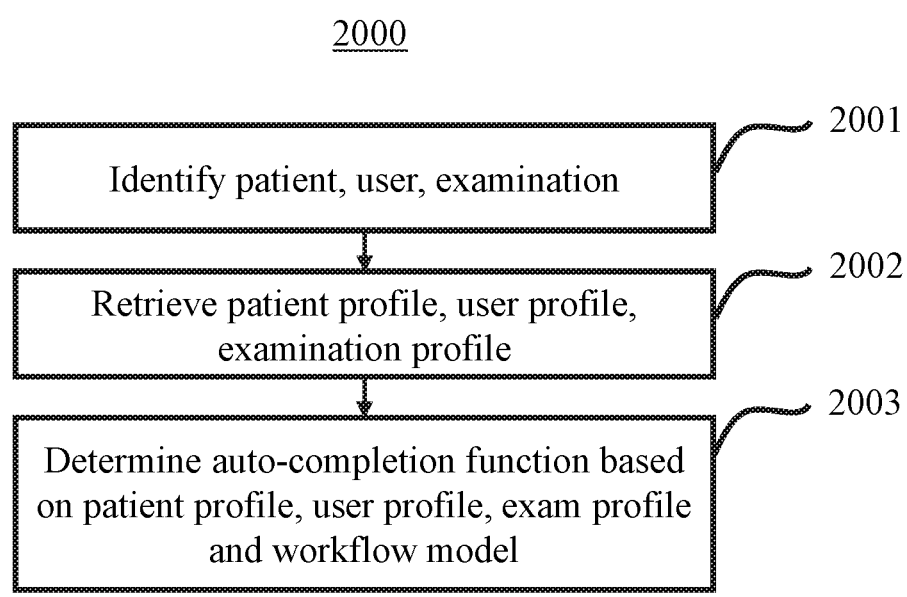
FIG. 20 is a flowchart of an exemplary process for using the model of workflow according to some embodiments.

FIG. 20 is a flowchart of an exemplary process 2000 for applying the workflow model, which may be used in step 303 of process 300 illustrated in FIG. 3, according to some embodiments.

At 2001, processor 202 may identify a patient, a user, and/or an examination. In some embodiments, processor 202 may identify the user, and/or the patient from a patient demographic page. In some embodiments, processor 202 may identify the user or patient from a hospital network. For example, processor 202 may identify the user, and/or the patient from a schedule (e.g., a user schedule, a patient schedule, an examination schedule, etc.) in the hospital network.

At 2002, processor 202 may retrieve the patient profile, the user profile, and/or the examination profile. In some embodiments, the user profile, the patient profile, the examination profile may include personal data associated with a user, a patient, and/or an examination. Merely by way of example, the user profile may include a user's identity, a class to which a user belongs, and/or a user's preferences. The patient profile may include a patient's identity and/or a patient's preferences. The examination profile may include an examination type, an examination preferences, etc. In some embodiments, the user and/or patient may be classified or grouped into one or more classes according to their usage patterns, user behavior, workflow history, demographics, proficiency, location, age, educational background, physical condition, mental condition, or the like, or the combination thereof.

In some embodiments, processor 202 may identify a class to which the user belongs (e.g., pathologist, gastroenterologist, cardiologist, etc.). Processor 202 may further present a workflow interface and/or workflow sequence customized to the class to which the user belongs according to certain rules or criteria. For example, the rule or criteria could be the most common usage pattern in that class of users, or it may be the most efficient usage pattern in that class of users, etc. The efficiency of usage pattern may be determined based on the time being used (e.g., used by that class of users over a period of time or the shortest time used by that class of users), the steps involved (e.g., the fewest steps used), diagnosis accuracy, or other efficiency measures.

At 2003, processor 202 may determine an auto-completion function based on the user, and/or the user preferences, and/or the workflow model. In some embodiments, the auto-completion function may be determined based on the patient profile, the user profile, or the examination profile. In some embodiments, the auto-completion function may include at least one of a suggested trace, a suggested waveform, a suggested measurement, a suggested text field, or the like, or any combination thereof. In some embodiments, the auto-completion function may be replaced by any other workflow function. The workflow function may be determined according to certain rules or criteria. For example, the rules or criteria may be based on the statistics and/or efficiency of the workflow function for users (a user or a class of users). In some embodiments, the statistics may include a frequency of usage for an individual user, a class of users, or a plurality of classes of users. In some embodiments, the efficiency may be determined by one or more of time consumption for manipulating the workflow function, number of used steps, number of pressed keys, ratings from users, accuracy in diagnosis or treatment, or any other measures. In some embodiments, the auto-completion function may be displayed to the user. In some embodiments, other workflow functions may be displayed to the user. The workflow function may be presented as a workflow interface or a workflow sequence to the user according to the rules or criteria described above.

In some embodiments, when the user saves an image and/or a clip, processor 202 may present an option for the user to give a feedback on image quality. In some embodiments, storage 203 may store the preset configuration and/or data of workflow saved by the user. In some embodiments, processor 202 may present the previously saved workflow configuration and/or data to the user. In some embodiments, processor 202 may present a recommendation of a most common workflow preset to the user. The most common workflow preset may be chosen by the frequency of usage or probability for the user or similar users. Alternatively or additionally, the most common workflow preset may be chosen based on the frequency of usage or probability for the patient or similar patients. Alternatively or additionally, the most common workflow preset may be chosen based on the frequency of usage or probability of the examination or similar examinations.

In some embodiments, storage 203 may store the user's operation steps and sequence information in the workflow. In some embodiments, processor 202 may allow user to edit and/or save their operation steps as a workflow preset for himself or herself, a group of particular (or similar) users, etc. In some embodiments, a saved workflow preset may be selected and used by the user, other users in the same class with the user, or the group of particular users. In some embodiments, a saved workflow preset may be fed into processor 202 as a training set to evolve or update the workflow model. In some embodiments, a saved workflow preset may be stored by storage 203 and may be used to update the user profile. A saved workflow preset may also be added to workflow data collection for user workflow statistics, which may be used to generate a new workflow and/or update a previously generated workflow model. In some embodiments, processor 202 may present a most common next step option to anticipate the next operation tool that the user will likely use.

In some embodiments, processor 202 may loop one or more steps in process 2000 to obtain a model. In some embodiments, processor 202 may implement one or more steps in process 2000 consecutively, or in parallel, or in any other orders.

Figure 21:
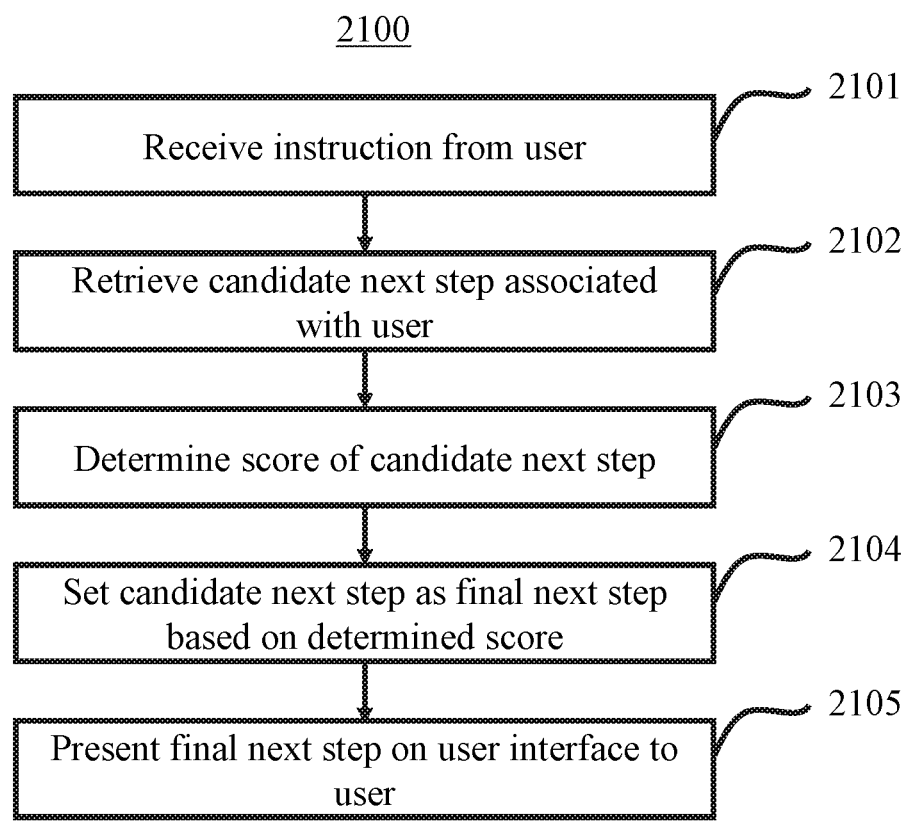
FIG. 21 is a flowchart of an exemplary process of user interface customization according to some embodiments.

In some embodiments, process 2000 may be performed according to an exemplary process for customizing the workflow illustrated in FIG. 21. FIG. 21 is a flowchart of an exemplary process 2100 for customizing workflow according to some embodiments.

At 2101, processor 202 may receive an instruction from a user. At 2102, processor 202 may retrieve (or generate ad-hoc) a candidate next step associated with the user. In some embodiments, the user may include an individual user and/or a group of users.

At 2103, processor 202 may determine the score of the candidate next step. In some embodiments, the score of the candidate next step may be represented as a ranking, a frequency of usage, a probability of the candidate next step, etc. Merely by way of example, for the user A, after identifying a LV view, the frequency of usage for the candidate next step to detect and trace a border may be 78%; the frequency of usage for the candidate next step to bring up color Doppler may be 9%.

At 2104, processor 202 may set the candidate next step as a final next step based on the determined score of the candidate next step. In some embodiments, processor 202 may set the candidate next step having a certain score (e.g., a highest frequency of usage, a lowest frequency of usage, a middle frequency of usage, a top ranking, a middle ranking, a low ranking, etc.) as final next step. In some embodiments, processor 202 may customize the workflow based on a most often usage pattern. For example, processor 202 may set the candidate next step to detect and trace a border having the highest frequency of usage of 78% as the final next step when the user identifies a LV view. In some embodiments, processor 202 may determine more than one final next steps.

At 2105, processor 202 may present the one or more final next steps on the user interface to the user. In some embodiments, processor 202 may present the final next step(s) with the certain score(s) (e.g., the certain frequency of usage, the certain probability, a certain ranking, etc.). For example, processor 202 may present the final next step to detect and trace a border when the user identifies a LV view, which has the highest probability on the user interface. In some embodiments, processor 202 may present an option for the user to select a next step among a number of next steps. For example, processor 202 may present a drop-down menu of the next step for the user to select one of the next steps. In some embodiments, processor 202 may present an optional "most common practice" workflow configuration to the user based on the data collected from the user, and/or a group of similar users.

In some embodiments, processor 202 may loop one or more steps in process 2100 to obtain a model. In some embodiments, processor 202 may implement one or more steps in process 2100 consecutively, or in parallel, or in any other orders.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "block," "module," "engine," "unit," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 1703, Perl, COBOL 1702, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution—e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claimed subject matter may lie in less than all features of a single foregoing disclosed embodiment.

What is claimed is:

1. A computing system, comprising:
   a memory configured to store instructions; and
   one or more processors configured to execute the instructions to:
   receive data relating to an image;
   determine one or more features from the data;
   obtain an enhancement model; and
   enhance the image based on the one or more features and the enhancement model;
   wherein the enhancement model is obtained based on a process including the following steps:
   obtaining a preliminary enhancement model;
   generating the enhancement model based on an actual output of the preliminary enhancement model and a desired output.

2. The computing system of claim 1, wherein the enhancement model is obtained based on a process further including the following steps:
   receiving historical data as an input;
   determining a desired output;
   obtaining the preliminary enhancement model based on the input and the desired output;
   determining the actual output of the preliminary enhancement model based on the input and the enhancement preliminary model;
   determining error criteria between the actual output of the preliminary enhancement model and the desired output; and
   generating the enhancement model by updating the preliminary enhancement model based on the error criteria.

3. The computing system of claim 2, the one or more processors are further configured to execute the instructions to automatically determine one or more training sets for training the preliminary enhancement model based on the historical data.

4. The computing system of claim 3, wherein the one or more training sets include at least one of a spatial feature or a temporal feature.

5. The computing system of claim 1, wherein the one or more processors are further configured to:
   determine one or more user preferences; and
   enhance the image based on the one or more features, the one or more user preferences, and the enhancement model.

6. The computing system of claim 5, wherein the one or more user preferences are determined from a user profile, the one or more user preferences including one or more imaging parameters in which the user is interested.

7. The computing system of claim 6, wherein the one or more processors are further configured to:
   segment the image based on the one or more features and a segmentation model.

8. The computing system of claim 7, wherein the one or more processors are further configured to:
   receive the segmented image;
   determine one or more segment features from the segmented image; and
   determine one or more values of the one or more imaging parameters based at least in part on the segmented image, the one or more user preferences, and the enhancement model.

9. The computing system of claim 1, further comprising a scanner configured to acquire the image, wherein the one or more processors are further configured to execute one or more of the instructions during a down-time of the scanner.

10. The computing system of claim 1, wherein the one or more processors are implemented on a cloud server or on a local computing device attached to a scanner that captures the image.

11. The computing system of claim 1 is an ultrasound imaging system.

* * * * *